US009782090B1

(12) United States Patent
Silverman

(10) Patent No.: US 9,782,090 B1
(45) Date of Patent: *Oct. 10, 2017

(54) METHOD AND SYSTEM ENABLING PHOTOPLETHYSMOGRAPH MEASUREMENT OF VOLUME STATUS

(71) Applicant: David G Silverman, West Redding, CT (US)

(72) Inventor: David G Silverman, West Redding, CT (US)

(*) Notice: Subject to any disclaimer, the term of this patent is extended or adjusted under 35 U.S.C. 154(b) by 79 days.

This patent is subject to a terminal disclaimer.

(21) Appl. No.: 14/511,306

(22) Filed: Oct. 10, 2014

Related U.S. Application Data

(63) Continuation-in-part of application No. 14/460,082, filed on Aug. 14, 2014, now abandoned, and a continuation-in-part of application No. 12/059,383, filed on Mar. 31, 2008, now Pat. No. 8,961,932.

(60) Provisional application No. 61/865,746, filed on Aug. 14, 2013, provisional application No. 61/889,780, filed on Oct. 11, 2013, provisional application No. 61/927,668, filed on Jan. 15, 2014, provisional application No. 60/920,823, filed on Mar. 30, 2007, provisional application No. 61/889,780, filed on Oct. 11, 2013, provisional application No. 61/927,668, filed on Jan. 15, 2014.

(51) Int. Cl.
*A61K 49/00* (2006.01)
*A61B 5/0295* (2006.01)
*A61B 5/029* (2006.01)
*A61B 5/02* (2006.01)
*A61B 5/00* (2006.01)

(52) U.S. Cl.
CPC ........ *A61B 5/0295* (2013.01); *A61B 5/02007* (2013.01); *A61B 5/029* (2013.01); *A61B 5/6815* (2013.01)

(58) Field of Classification Search
USPC ........................................................ 424/9.1
See application file for complete search history.

(56) References Cited

U.S. PATENT DOCUMENTS

| | | | |
|---|---|---|---|
| 5,466,465 | A | 11/1995 | Royds et al. |
| 6,417,205 | B1 | 7/2002 | Cooke et al. |
| 6,485,431 | B1 | 11/2002 | Campbell |
| 6,656,147 | B1 | 12/2003 | Gertsek et al. |
| 6,741,895 | B1 | 5/2004 | Gafni et al. |
| 2005/0249774 | A1 | 11/2005 | Pauletti et al. |
| 2008/0241199 | A1 | 10/2008 | Silverman |

OTHER PUBLICATIONS

Anderson, T.J., et al., "Close Relation of Endothelial Function in the Human Coronary and Peripheral Circulations", JACC, 1995, 26(5): 1235-1241.

Anderson, T.J., et al., "A Comparative Study of Four Anti-Hypertensive Agents on Endothelial Function in Patients with Coronary Disease", J Am Coll Cardiol 1998, 31:327A, Abst.
Anderson, T.J., et al., "Systemic Nature of Endothelial Dysfunction in Atherosclerosis", Am J Cardiol, 1995, 75:71B.
Anderson, T.J., et al., "The Effect of Cholesterol-Lowering and Antioxidant Therapy on Endothelium-Dependent Coronary Vasomotion". N Engl J Med 1995, 332:488.
Benjamin, "Hypertension", 1995; 25: 918-923.
Bjarnason, et al., "Contact Dermatitis" Sep. 1998; 39(3):112-8.
Bossaller, C., et al., "Impaired Muscarinic Endothelium-Dependent Relaxation and Cyclic Guanosine 5'-Monophosphate . . . ", Journal of Clinical Investigation, 1987, 79:170-4.
Braverman, I.M, et al., "Topographic Mapping of the Cutaneous Microcirculation Using Two Outputs of Laser-Doppler Flowmetry . . . " Microvascular Research, Jul. 1992, 44(1):33-48.
Christen, S, et al al., "Dose-Dependent Vasodilatory Effects of Acetylcholine and Local Warming on Skin Microcirculation", Journal of Cardiovascular Pharmacology, 2004, 44:659-64.
"Demise of a Blockbuster Drug Complicates Pfizer's Revamp", Wall Street Journal, Dec. 4, 2006.
Drexler, H., Zeiher, A.M., Progression of Coronary Endothelial Dysfunction in man and its Potential Clinical Significance, Basic Research in Cardiology. 1991, 2:223-32.
Droog, E.J., Sjoberg, F., "Nonspecific Vasodilatation During Transdermal Iontophoresis-the Effect of Voltage Over the Skin", Microvascular Research, 2003, 65:172-8.
Ferrell, W.R., et al., "Elimination of Electrically Induced Iontophoretic Artefacts: Implications for Non-Invasive . . . ", Journal of Vascular Research, 2002, 39:447-55.
Furchgott, R.F., Zawadzki, J.V., "The Obligatory Role of Endothelial Cells in the Relaxation of Arterial Smooth Muscle by Acetylcholine", Nature, 1980, 288: 373-6.
Holowatz, L.A., et al., "Mechanisms of Acetylcholine-Mediated Vasodilatation in Young and Aged Human Skin", Journal of Physiology, 2005, 563:965-73.
Kaski, "Circulation", 74, No. 6, 1255-1265, 1986.
Khan, F., et al., "Influence of Vehicle Resistance on Transdermal Iontophoretic Delivery of Acetylcholine and Sodium . . . ", Journal of Applied Physiology, 2004, 97:883-7.
Ledger, P., "Skin Biological Issues in Electrically Enhanced Transdermal Delivery", Advanced Drug Delivery Reviews. 1991, 9:289-307.
Mo, C., Stout, R.G., Shelley, K.H., Tantawy, H., Silverman, D.G., Acute Microcirculatory Effects of Nicotine in Non-Smoking Volunteers, Anesthesiology 2004, 101:A246.
Morris, S.J., Shore, A.C., Tooke, J.E., "Responses of the Skin Microcirculation to Acetylcholine and Sodium Nitroprusside in Patients with NIDDM", Diabetologia, 1337:38-44.

(Continued)

*Primary Examiner* — Devang Thakor
(74) *Attorney, Agent, or Firm* — Welsh Flaxman & Gitler LLC

(57) ABSTRACT

A method enables photoplethysmograph measurement of volume status. The method includes the steps of converting photoplethysmograph voltages to volume measurements and characterizing a local microcirculation as a microcosm in a manner allowing a photoplethysmograph to facilitate non-invasive monitoring of systemic status.

21 Claims, 31 Drawing Sheets

(56) References Cited

OTHER PUBLICATIONS

Nissen, A., et al., "Consistency of Laser Doppler Assessments of Vasoreactivity", American Society of Anesthesiologists, 2006, 2A244.

Nissen, A.F., et al., "Sensitivity of Acetylcholine and Nitroglycerin-Induced Vasodilation to Endothelial Impairment", Anesthesiology, 2007, 107:A291.

Noon, J.P., et al., "Studies with Iontophoretic Administration of Drugs to Human Dermal Vessels in Vivo: Cholinergic . . . ", Br J Clin Pharmacol, 1998, 45:545-50.

Opazo Saez, A.M., et al., "Laser Doppler Imager (LDI) Scanner and Intradermal Injection for InVivo . . . ", British Journal of Clinical Pharmacology, May 2005, 59(5):511-519.

Peters, E.J., et al., "The Benefit of Electrical Stimulation to Enhance Perfusion in Persons with Diabetes Mellitus", Journal of Foot & Ankle Surgery, 1998, 37:396-400.

Saez, et al., "Br J Clin Pharmacol", 2005, 59)5): 511-19.

Scheindlin, "Molecular Interventions", Dec. 2004,; 4(6): 308-312.

Schonberger, R.B., et al., "Topical Non-Iontophoretic Application of Acetylcholine and Nitroglycerin . . . ", Yale J Biol Med, 2006, 78:229-235.

Silverman, D.G., et al., "Detection and Characterization of Cholinergic Oscillatory Control in the Forehead Microvasculature . . . ", Microvasc Res, 2001, 61:144-7.

Silverman, D.G., et al., "Distinction Between Aropine-Sensitive Control of Microvascular and Cardiac Oscillatory Activity", Microvasc Res, 2002, 63:196-208.

Suzuki, "Stroke", 1993; 24: 1049-1053.

Thanyasiri, P, et al., "Endothelial Dysfunction Occurs in Peripheral Circulation of Patients with . . . ", American Journal of Physiology Heart & Circulatory Physiology, 2005, 289.

Wang, S., Omar, W., Awad, A., Scannell, M., Silverman, D.G., "Direct and Reflexive Autonomic Effects of Acupuncture in Healthy Subjects", Int Anesth Res Soc, 2002, S-215.

Wardell, K., et al., "Spatial Heterogeneity in Normal Skin Perfusion Recorded with Laser Doppler Imaging and Flowmetry", Microvascular Research, Jul. 1994, 48(1):26-38.

Wilkin, J.K., "Poiseuille, Periodicity, and Perfusion: Rhythmic Oscillatory Vasomotion in the Skin", The Journal of Investigative Dermatology, Aug. 1989, 93(2): 113S-118S.

Yoshida, M., et al., "Impaired Forearm Vasodilatation by Acetylcholine in Patients with Hypertension", Heart & Vessels, 1991, 6:218-23.

Kraitl (J. Opt. A: Pure Appl. Opt. 7 (2005) S318-S324).

McGrath (Anesth Analg. Feb. 2011 112(2): 368-74).

| | |
|---|---|
| PRIMARY OBJECTIVE: INTRODUCE $AC_{rest}$MULTIPLES to eliminate impacts of attenuation and interdevice differences within and among subjects | |
| If AC is isolated by high pass (eg, >0.5 Hz) filtering, a preferred embodiment entails establishing $AC_{rest}$VOLTAGE as = mean AC height of a selected section of filtered tracing @rest | If $\Delta$AC is determined as peak-to-trough difference of individual pulses, a preferred embodiment entails establishing $AC_{rest}$VOLTAGE (= height of single beat or mean height of multiple beats @rest |
| CONVERT ANY & ALL PPG VOLTAGES TO # of $AC_{rest}$MULTS, WHERE: # OF $AC_{rest}$MULTS = GIVEN PPG VOLTAGE x '1 $AC_{rest}$MULT/$AC_{rest}$VOLTAGE', WHICH MAY BE EXPRESSED AS: "=GIVEN PPG VOLTAGE x '1 $AC_{rest}$MULT/$AC_{rest}$VOLTAGE"    or as    "= GIVEN PPG VOLTAGE/$AC_{rest}$VOLTAGE" | |
| CONVERT ANY & ALL AC VOLTAGES TO # of $AC_{rest}$MULTS: = 'GIVEN AC VOLTAGE' x '1 $AC_{rest}$MULT/$AC_{rest}$VOLTAGE' Note: if calibrating measurement not attainable @rest, then can be achieved if one knows the status of the systemic stroke volume (SV) (e.g., by echocardiographic measurement) – see text. | Determine magnitude of DC component of PPG tracing in accordance with prior art methods such as measuring: mean of the raw signal; mean of signal filtered to eliminate AC component (e.g., low=pass, <0.5 Hz); and trough between individual beats generated by peak analysis. CONVERT ANY & ALL DC VOLTAGES TO # of $AC_{rest}$MULTS: = 'GIVEN DC VOLTAGE' x '1 $AC_{rest}$MULT/$AC_{rest}$VOLTAGE' |
| QUANTIFY CHANGE IN AC ($\Delta$AC) as # of $AC_{rest}$MULTS: =#$AC_{rest}$MULTS for $AC_{NEW}$' – '#$AC_{rest}$MULTS for $AC_{PRE}$'; or = '$\Delta$AC VOLTAGE' x '1 $AC_{rest}$MULT/$AC_{rest}$VOLTAGE' | QUANTIFY CHANGE IN DC ($\Delta$DC) as # of $AC_{rest}$MULTS: = '#$AC_{rest}$MULTS for $DC_{NEW}$' – '#$AC_{rest}$MULTS for $DC_{PRE}$'; or = '$\Delta$DC VOLTAGE' x '1 $AC_{rest}$MULT/$AC_{rest}$VOLTAGE' |
| Ratio of new or $\Delta$AC in $AC_{PRE}$ to $AC_{PRE}$ in $AC_{rest}$MULTS (i.e., relative change of AC): =#$AC_{rest}$MULTS of $AC_{NEW}$ or $\Delta$AC/#$AC_{rest}$MULTS of $AC_{PRE}$ | Isolation of DCblood from DCbackground is required to assess relative changes of DC – see text and Figures 4 and 6. |

Figure 2

| AN OBJECTIVE OF PRESENT INVENTION: INTRODUCTION OF PHOTOPLETHYSMOGAPHIC COMPLIANCE ASSESSMENT IN $AC_{rest}$ MULTIPLES/mmHg | | | |
|---|---|---|---|
| As per Figure 2 | As per Figure 2 | | |
| As per Figure 2 | | As per Figure 2 | |
| | | | CONVERT DC in $AC_{REST}$MULT TO DCcompliance in $AC_{REST}$MULTS/mmHg = '#$AC_{REST}$MULTS for given DC time point or $\Delta DC$'/17.5mmHg |
| CONVERT AC in $AC_{REST}$MULTS to ACcompliance in $AC_{REST}$MULTS/mmHg = '#$AC_{rest}$MULTS for given AC time point or $\Delta AC$'/65mmHg | | | If an embodiment to distinguish DCblood has been implemented (see text and Figures 4 and 6), then one can determine ratio of new or $\Delta$ DCcompliance to pre intervention DC ($DC_{pre}$) and/or DCcompliance (DCcompliance$_{pre}$) |
| Can determine ratio of new or $\Delta$ACcompliance to ACcompliance$_{rest\ or\ pre}$ (all in $AC_{rest}$Mult/mmHg) or to $AC_{pre}$ or $AC_{rest}$ | | | |

Figure 3

| AN OBJECTIVE OF PRESENT INVENTION: ALLOW FOR ELIMINATION OF BACKGROUND FROM DC DETERMINATIONS | | | |
|---|---|---|---|
| As per Figure 2 | As per Figure 2 | As per Figure 2 | Ratio of $DCblood_{NEW}$ or $\Delta DC$ in $AC_{rest}MULTS$ to $DCblood_{PRE}$ in $AC_{rest}MULTS$ (i.e., relative change of DCblood independent of DCbackgound): <br> = #$AC_{rest}$MULTS of $DCblood_{NEW}$ / #$AC_{rest}$MULTS of $DCblood_{PRE}$ or <br> = $\Delta DC$/#$AC_{rest}$MULTS of $DCblood_{PRE}$ <br> Note: because it is independent of background, $\Delta DC = \Delta DCblood$ |
| As per Figure 2 | | | |
| As per Figure 2 | | | |

Figure 6

| AN OBJECTIVE OF PRESENT INVENTION: INTRODUCTION OF PHTOPLETHYMOGRAPHIC MEASURES OF ARTERIAL AND VENOUS VOLUME: ||
|---|---|
| As per Figure 2: If AC is isolated by high pass (eg, >0.5 Hz) filtering, a preferred embodiment entails establishing $AC_{rest}$VOLTAGE as = mean AC height of a selected section of filtered tracing @rest | As per Figure 2: If AC is determined as peak-to-trough difference of individual pulses, a preferred embodiment entails establishing $AC_{rest}$VOLTAGE = height of single beat or mean height of multiple beats @rest |
| Apply Plethysmographic Signal to Volume (in mlppg) CONVERSION FACTOR (CF) ||
| For Data already converted to $AC_{rest}$Mults:<br>• PPG signal (in $AC_{rest}$Mults) to volume (in $ml_{PPG}$) CF is $SV_{rest}$Volume/$1AC_{rest}$Mult<br>• Volume (in $ml_{PPG}$) for a given AC or DCblood measurement:<br>= current # of $AC_{rest}$Mults x CF<br>=current # of $AC_{rest}$Mults x '$SV_{rest}$ in ml/$1AC_{rest}$Mult'<br>• If $SV_{rest}$ is known, e.g. 125 ml, then<br>= current # of $AC_{rest}$Mults x '125 ml/$1AC_{rest}$Mult' | For Data in Volts:<br>• PPG signal (in volts) to volume (in $ml_{PPG}$) CF is $SV_{rest}$Volume/$AC_{rest}$Voltage<br>• Volume (in $ml_{PPG}$) for a given AC or DCblood measurement:<br>= current Voltage x CF<br>=current Voltage x '$SV_{rest}$ in ml/$AC_{rest}$Voltage<br>• If $SV_{rest}$ is known, e.g. 125 ml, then<br>= current Voltage x '125 ml/$AC_{rest}$Voltage' |

Figure 12

SAMPLE CONVERSION OF VOLTAGE TO VOLUME (ml$_{PPG}$)
when AC$_{rest}$ Voltage is the AC Calibration Voltage Sample Values:

SV$_{rest}$ = 125 ml (by echocardiography for given subject),
AC$_{rest}$ = 0.2 volts;
ΔAC = 0.04 volts = 0.2 AC$_{rest}$Mults;
ΔDC = 1.2 volts = 6 AC$_{rest}$Mults a) Using voltages :

SV$_{rest}$/AC$_{rest}$ conversion factor = 125 ml/0.2 volts;
ΔSV calculation: '0.04 volts' x '125 ml/0.2 volts' = 25 ml$_{ppg}$;
ΔVenous volume calculation: '1.2 volts' x '125 ml/0.2 volts' = 750 ml$_{PPG}$.

or b) Using AC$_{rest}$Mults:

SV$_{rest}$/AC$_{rest}$ conversion factor = 125 ml/1AC$_{rest}$Mult;
ΔSV calculation: '0.2 AC$_{rest}$Mults' x '125 ml/1 AC$_{rest}$Mult' = 25 ml$_{ppg}$;
ΔVenous volume calculation: '6 AC$_{rest}$Mults' x125 ml/1 AC$_{rest}$Mult = 750 ml$_{PPG}$ If AC$_{rest}$ is not the Calibrating Voltage, then additional steps are required to calibrate the photoplethysmographic signal before it can be utilized for the conversion factor (explained in text)

Figure 13

| | Millivolts | $AC_{rest}$ $Mults^a$ | PPG-derived Blood Volume (in $ml_{PPG}$) during pre and at light-headedness: $= Voltage \times$ '120 ml/$AC_{rest}$ Voltage'; or $= $ '# of$_{rest}$ Mults' $\times$ '120ml/1 $AC_{rest}$ Mult' |
|---|---|---|---|
| LBNP PHASE | | | |
| ACpreLBNP (equivalent to $AC@$rest) | 20 | 1 | 120 |
| $AC_{@light\text{-}headedness}$ | 8 | 0.4 | 48 |
| $\Delta AC$ | -12 | -0.6 | -72 |
| $DCblood_{pre}$ | 680 | 34 | 4080 |
| $DCblood_{@light\text{-}headedness}$ | 460 | 23 | 2760 |
| $\Delta DC$ | -220 | -11 | -1320 |
| RESTORATION PHASE | | | |
| $AC@$start of restoration (not equivalent to $AC_{rest}$) | 8 | 0.4 | 48 |
| $AC_{rest}$ (as per preLBNP) | 20 | 1 | 120 |
| $AC@$end of restoration | 24 | 1.2 | 144 |
| $\Delta AC$ | 16 | 0.8 | 96 |
| $DC@$start of restoration | 460 | 23 | 2760 |
| $DC@$end of restoration | 760 | 38 | 4560 |
| $\Delta DC$ | 300 | 15 | 1800 |

Figure 15

Decline in volume based upon
$SV_{rest}$ Volume/1 $AC_{rest}$Mult conversion factor Decline in volume based upon
$SV_{rest}$ Volume/$AC_{rest}$ Voltage conversion factor Subject undergoing lower body negative pressure. Upper panel is raw signal; Lower panel isolates AC component.

Restoration of AC and DC in five subjects

Differences from LBNP-induced nadir in $AC_{rest}$Mults during return of sequestered blood ΔAC/ΔDC during restoration of sequestered blood Delineation of Frank-Starling relationships based upon AC and DC measurements in accordance with described embodiments Subject who developed light-headedness during blood restoration at 1822 sec.

Subject who developed hypotension during early phase of blood restoration.

| Finger vs Ear | Finger Height relative change | Ear Height relative change | Finger height relative change/Ear height relative change | subtracting ear DC from Finger DC | Finger DC change in AC units | Ear DC change in AC units | Finger DC change in AC units/Ear DC change in AC units |
|---|---|---|---|---|---|---|---|
| Awad-52*-70 | 0.73368 | 0.478094 | 1.534594492 | 4.466054 | 7.76978417 | 3.30373 | 2.351821768 |
| Blizzard 10 | 0.89942 | 0.65054 | 1.382573476 | 1.276546 | 4.154738883 | 2.878193 | 1.443523361 |
| Chris | 0.441089 | 0.464874 | 0.948834547 | 1.21586 | 3.118826249 | 1.912402 | 1.635776259 |
| David | 0.588324 | 0.253968 | 2.316527672 | 5.487504 | 7.266868884 | 1.779365 | 4.083967323 |
| Don | 0.533384 | 0.475632 | 1.121423194 | 19.18701 | 22.6707598 | 3.483755 | 6.507565244 |
| Ed | 0.32155 | 0.149082 | 2.156872774 | 5.364024 | 6.25556428 | 0.89154 | 7.016579548 |
| Joel-50*-65 | 0.456456 | 0.450153 | 1.014001331 | -1.36203 | 2.280660369 | 3.642638 | 0.626085729 |
| Michael 0923 | 0.455987 | 0.70578 | 0.646074918 | 16.3018 | 17.920552 | 1.418757 | 12.63116542 |
| Michael 0919-50*-65 | 0.423909 | 0.391224 | 1.083546049 | 3.899769 | 5.71761572 | 1.817847 | 3.145268525 |
| Nick-55*-65 | 0.619793 | 0.500998 | 1.237117115 | 4.354838 | 6.70014771 | 2.345309 | 2.856828939 |
| Rob | 0.669983 | 0.328966 | 2.036663221 | 0.850673 | 4.42343836 | 3.572766 | 1.238099251 |
| Sarah 10 | | | | | | | |
| Mean | 0.558507 | 0.440846 | 1.407109162 | 5.567458 | 8.02621236 | 2.458755 | 3.957800147 |
| std | 0.165405 | 0.160022 | 0.544175931 | 6.466673 | 6.38902625 | 0.964603 | 3.546302355 |
| median | 0.533384 | 0.464874 | 1.237117115 | | 6.25556428 | 2.345309 | 2.856828939 |

Figure 28

METHOD AND SYSTEM ENABLING PHOTOPLETHYSMOGRAPH MEASUREMENT OF VOLUME STATUS

CROSS REFERENCE TO RELATED APPLICATIONS

This application is a continuation-in-part of U.S. patent application Ser. No. 14/460,082, filed Aug. 14, 2014, entitled "METHOD AND SYSTEM ENABLING PHOTOPLETHYSMOGRAPH MEASUREMENT OF VOLUME STATUS," which is currently pending, which claims the benefit of U.S. Provisional Application Ser. No. 61/865,746, filed Aug. 14, 2013, entitled "CONVERTING PHOTOPLETHYSMOGRAPHIC VOLTAGE TO A VOLUME MEASUREMENT: UNIQUE APPLICATION OF THE AC COMPONENT TO NORMALIZE FOR SIGNAL ATTENUATION WITHIN AND AMONG SUBJECTS," U.S. Provisional Application Ser. No. 61/889,780, filed Oct. 11, 2013, entitled "CONVERTING PHOTOPLETHYSMOGRAPHIC (PPG) VOLTAGE TO A VOLUME MEASUREMENT: UNIQUE APPLICATION OF THE AC COMPONENT TO NORMALIZE FOR SIGNAL ATTENUATION, ESTABLISH A VOLTAGE TO VOLUME CONVERSION FACTOR AND ELIMINATE IMPACT OF BACKGROUND," and U.S. Provisional Application Ser. No. 61/927,668, filed Jan. 15, 2014, entitled "CONVERTING PHOTOPLETHYSMOGRAPHIC (PPG) VOLTAGE TO A VOLUME SIGNAL: ADDITIONAL MODIFICATIONS TO IMPROVE UTILITY IN CLINICAL AND INVESTIGATIVE SETTINGS, this application is also a continuation-in-part of U.S. patent application Ser. No. 12/059,383, entitled "'MICRO-PATCH'" FOR ASSESSMENT OF THE LOCAL MICROVASCULATURE AND MICROCIRCULATORY VASOREACTIVITY," filed Mar. 31, 2008, which is currently pending, which claims the benefit of U.S. Provisional Patent Application Ser. No. 60/920,823, filed Mar. 30, 2007, entitled "'MICRO-PATCH' FOR ASSESSMENT OF THE LOCAL MICROVASCULATURE AND MICROCIRCULATORY VASOREACTIVITY," and this application also claims the benefit of U.S. Provisional Application Ser. No. 61/889,780, filed Oct. 11, 2013, entitled "CONVERTING PHOTOPLETHYSMOGRAPHIC (PPG) VOLTAGE TO A VOLUME MEASUREMENT: UNIQUE APPLICATION OF THE AC COMPONENT TO NORMALIZE FOR SIGNAL ATTENUATION, ESTABLISH A VOLTAGE TO VOLUME CONVERSION FACTOR AND ELIMINATE IMPACT OF BACKGROUND," and U.S. Provisional Application Ser. No. 61/927,668, filed Jan. 15, 2014, entitled "CONVERTING PHOTOPLETHYSMOGRAPHIC (PPG) VOLTAGE TO A VOLUME SIGNAL: ADDITIONAL MODIFICATIONS TO IMPROVE UTILITY IN CLINICAL AND INVESTIGATIVE SETTINGS, all of which are incorporated herein by reference.

BACKGROUND OF THE INVENTION

1. Field of the Invention

The invention relates to a method and system enabling photoplethysmograph measurement of volume status.

2. Description of the Related Art

Assessments of impact on blood volume by challenges ranging from local application of a vasoactive agent to systemic blood loss share a common problem—how to effectively monitor the impacts noninvasively. Moreover, they may share a common solution—a heretofore unreported use of the photoplethysmograph (PPG, also referred to as photoplethymogram) to delineate local as well as systemic changes in pulsatile volume ("AC" which represents portion of the stroke volume (SV) delivered to the given site) and nonpulsatile volume ("DC," which represents the venous volume+arterial volume at given site, except for the portion of arterial volume that changes with each stroke volume, i.e., except for the AC).

Monitoring of local volume and flow has been thwarted by limitations. Thermometry is nonspecific; radionuclide and substrate sampling are invasive; laser Doppler flowmetry has high spatial heterogeneity (due to varying numbers of arterioles and capillaries in its 1 $mm^3$ sampling area); measurement of flow-mediated vasodilation measures changes in larger vessels in limited locations; strain gauge plethysmography is nonspecific and limited as to site of application; and, in the absence of methods and systems disclosed in accordance with the present invention, photoplethysmograph is confounded by attenuation (based on extinction coefficient of the media transversed by the transmitted light) and background (non-blood tissues). Moreover, none of the noninvasive techniques distinguishes arterial and venous volume; thus, they cannot fully characterize local physiologic impact and its relationship to arterial and venous components of the systemic circulation.

Monitoring of systemic volume likewise has been challenging, prompting a search for alternatives to invasive (and not consistently reliable) central venous and pulmonary artery pressure monitoring. When available, echocardiography often provides the gold standard, but preload measurements have been inconsistent and stroke volume measurements during lower body negative pressure (LBNP), a model of simulated blood loss, are disturbed by vacuum-induced changes in chest alignment; likewise for measures of thoracic impedance. Monitoring contour and magnitude of arterial pressure and photoplethysmograph waveforms are impacted by changes in local vascular tone; thus far, neither has quantified changes in venous volume. Although increases in ventilation-induced variations in intra-arterial and intra-venous waveforms can identify hypovolemia, they do not quantify volume status and the effectiveness of such monitoring is limited in the absence of positive pressure ventilation.

The monitoring limitations in the aforementioned settings have prompted investigations into mechanisms for improving interpretation of changes in the signal generated by the photoplethysmograph. The conventional wisdom has been that, although AC height trends with stroke volume, most potentially meaningful volume information within photoplethysmograph voltages is obscured by background, attenuation, inconsistencies among devices and regional vasomotor activity. Hence, analysis of individual photoplethysmograph beats typically entails voltage clamping and complex contour analysis. On a local level, investigators and clinicians have evaluated changes in pulse height attributable to ischemia, autonomic activity, and regional anesthetics. However, changes in arterial and venous volume have not been effectively distinguished and compared. Recent efforts to assess systemic volume have focused on ventilation induced variations of the photoplethysmograph waveform, such as plethysmographic variability index (PVI) and spectral-domain analysis of oscillatory activity at the respiratory frequency. However, and as noted above, these only provide relative assessments (i.e., they neither measure nor estimate actual volume), and they are confounded by rate, depth and pattern of respiration.

A major limitation to the use of the photoplethysmograph for these purposes is that commercial devices (e.g., for clinical monitoring) have autocentering and/or dynamic recalibrating algorithms that minimixe changes in voltages caused by what I believe to be important physiologic changes. This is because the commercial photoplethysmograms are components of pulse oximeters, designed to identify the time of arterial pulsation so as to determine arterial oxygen saturation; changes in the photoplethysmographic tracing have been considered "distracting." I believe that what others have considered noise is actually music hence, unless otherwise specified, all photoplethysmographic data shown herein are obtained using noncommercial devices without the aforementioned algorithms and the embodiments included herein are derived from said data.

SUMMARY OF THE INVENTION

It is, therefore, an object of the present invention to provide a method enabling photoplethysmograph measurement of volume status despite current limitations including those imposed by attenuation and background. The method includes the steps of converting photoplethysmograph voltages to multiples of a calibrating voltage and to voltage-derived volume measurements, thereby enabling characterization of a local microcirculation as a microcosm in a manner allowing a photoplethysmograph to facilitate non-invasive monitoring of systemic as well as local status.

It is also an object of the present invention to provide a method wherein the step of converting includes introducing an AC Calibration Voltage, defined herein as the measured voltage generated by the small portion of a cardiac stroke volume delivered to a given photoplethysmograph at a given site in a given subject at the time of calibration.

It is another object of the present invention that the AC Calibration Voltage be obtained under undisturbed baseline conditions (i.e., $AC_{rest}$Voltage is the basis for calibration).

It is a further object of the present invention to provide a method including the step of applying the $AC_{rest}$Voltage ($=AC_{rest}$Equivalent) in converting AC values at any and all time points for given photoplethysmograph at given site to $AC_{rest}$Multiples ($AC_{rest}$Mults).

It is a further object of the present invention to provide a method including the step of applying the $AC_{rest}$Voltage in comparing DC values for given photoplethysmograph at given site as $AC_{rest}$Mults.

It is a further object of the present invention to relate the $AC_{rest}$Voltage to a resting measurement of cardiac stroke volume (SV), wherein $SV_{rest}$Volume is measured by a method such as echocardiography or estimated based on known population data.

It is an additional object of the present invention to convert AC voltages and/or changes thereof that are multiples or fractions of the $AC_{rest}$Voltage to multiples or fractions of $SV_{rest}$Volume, as may be enabled by one of two conversion factors introduced herein:
  $SV_{rest}$Volume/1 $AC_{rest}$Mult conversion factor, if given AC reading is in $AC_{rest}$Mults; or
  $SV_{rest}$Volume/$AC_{rest}$Voltage conversion factor, if given AC reading is in volts.

It is an additional object of the present invention to convert DC voltages and/or changes thereof that are multiples or fractions of the $AC_{rest}$Voltage to multiples or fractions of $SV_{rest}$Volume, as may be enabled by a:
  $SV_{rest}$Volume/1 $AC_{rest}$Mult conversion factor, if given DC reading is in $AC_{rest}$Mults; or
  $SV_{rest}$Volume/$AC_{rest}$Voltage conversion factor, if given DC reading is in volts.

It is an additional object of the present invention to enable calibration at a time point other than @rest by relating AC voltage at given time point ($AC_{GivenTimePoint}$Voltage) to a measurement of stroke volume (or alternative parameter) at the given time point (e.g. $SV_{GivenTimePoint}$Volume). This may either:
  generate $AC_{GivenTimePoint}$Mults; and/or
  enable the $AC_{-rest}$ Voltage and hence $AC_{-rest}$Mults to be obtained by extrapolating according to the $SV_{GivenTimePoint}/SV_{rest}$ ratio
  (where $SV_{rest}$ is either estimated or already was measured under baseline conditions).

It is also an object of the present invention to provide a method wherein arterial and/or venous compliance can be determined It is also an object of the present invention to provide a method wherein the relationship between changes in DC and AC can be used to provide Frank-Starling relationships as may occur during volume loss and replacement.

It is also an object of the present invention to provide a method wherein the AC Calibration Voltage for a photoplethysmogaph placed on the Ear. is determined based upon Ear measurements.

It is another object of the present invention to provide a method wherein the AC Calibration Voltage for a photoplethysmograph placed on the forehead is determined based upon Forehead measurements.

It is another object of the present invention to provide a method wherein the AC Calibration Voltage for a photoplethysmograph placed on an alternative site such as the finger of nasal ala is determined based upon respective measurements.

It is an additional object of the present invention to provide a method for noninvasive measurement of arterial and venous components of the circulation utilizing a photoplethysmograph at one or more sites for independent and comparative assessment in clinical and investigative settings.

It is addition an object of the present invention to provide a method for assessing physiologically meaningful values (i.e., $AC_{rest}$Mults and $SV_{rest}$Mults as opposed to voltages) by spectral-domain analysis.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a flow chart for establishing $AC_{rest}$Multiples ($AC_{rest}$Mults) in accordance with the present invention.

FIG. 3 is a flow chart for establishing $AC_{rest}$Mults in accordance with an alternate embodiment of the present invention that calculates arterial and venous compliance.

FIG. 6 is a flow chart for establishing AC$_{rest}$Mults in accordance with an alternate embodiment of the present invention wherein conversion of DC to DCblood enables measurement of relative as well as absolute changes.

FIG. 12 is a flow chart for converting photoplethysmographic readings to volume measurements in accordance with an alternate embodiment of the present invention.

FIG. 13 shows a sample conversion of voltage to volume and AC$_{rest}$Mults to volume.

FIG. 15 shows a table of hypothetical measurements during hypovolemia (simulated blood loss) in accordance with the present invention. Prior to initiation of LBNP, the baseline (@rest) AC and DC readings obtained on the car are 20 millivolts and 680 mvolts, respectively. SV was measured as 120 ml byechocardiography. At the time of onset of LBNP-induced light headedness, AC and DC have decreased to 8 mv and 460 mv. Upon restoration, they overshoot to 24 mv and 760 mv.

FIG. 28 shows the data obtained during concurrent monitoring of plethysmographic signals at the Ear and Finger during lower body negative pressure.

DESCRIPTION OF THE PREFERRED EMBODIMENTS

Figure 1:
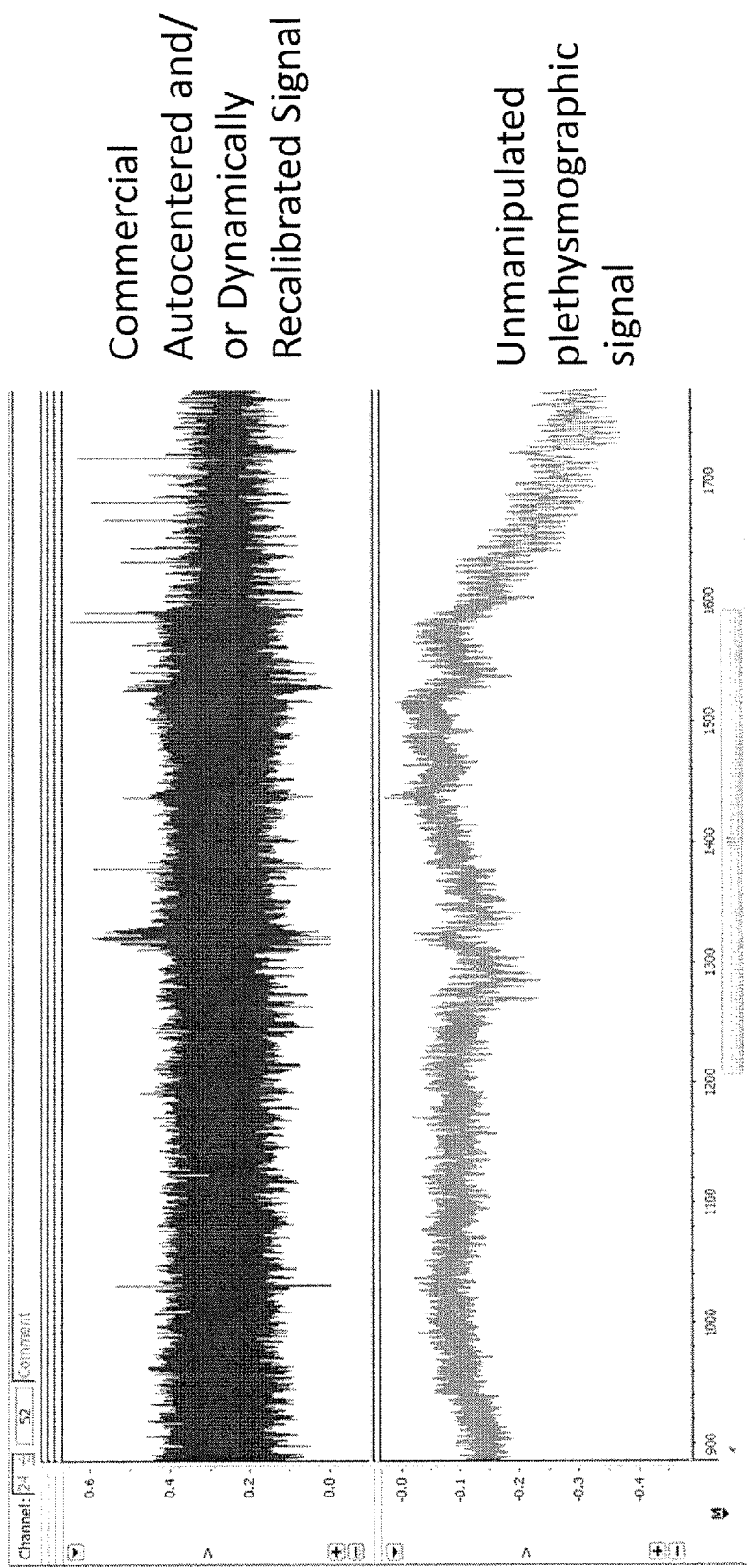
FIG. 1 shows autocentered and non-autocentered plethysmographic tracings during baseline period followed by simulated blood loss in accordance with the established model of applying lower body negative pressure utilized herein. Data encompasses interval between ~900 and ~2000 seconds, such that oscillations (predominantly at the respiratory frequency of ~0.2 Hz) but not individual beats (at 1 to 2 Hz) are discernible.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

With reference to the accompanying figures, a system and method enabling photoplethysmograph monitoring and measurement of volume status by establishing the "AC Calibration Voltage," which is the measured voltage generated by the small portion of a cardiac stroke volume delivered to a given photoplethysmograph at a given site in a given subject at the time of calibration, of a given photoplethysmograph at a given site under resting conditions so as to convert all voltages (photoplethysmographic (PPG) signal and its AC and DC components) to herein introduce "AC Multiples" of the AC Calibration Voltage, wherein the value (or number) of AC Multiples represents the ratio of the measured photoplethysmograph voltage to the resting photoplethysmographic voltage as explained below in greater detail. The present system and method further provides for the conversion of photoplethysmograph voltages to volume measurements and enables the local microcirculation to be characterized as a microcosm such that the photoplethysmograph can serve as a noninvasive window for monitoring systemic as well as local cardiovascular (vessel physiology, pharmacology and volume) status. By introducing AC MULTIPLES the impact of attenuation is eliminated. Further, a common mechanism is provided for conversion to heretofore unattainable common units for within parameter & interparameter (e.g., AC & DC), within site & intersite, and within subject & intersubject measurements and comparisons (with common units and elimination of impact of attenuation).

With the foregoing in mind, the present invention seeks to discern the music within the cacophony of photoplethysmograph variables based in part upon a foundation of known, but at times under-appreciated, features of photoplethysmograph monitoring pertaining to:

a) signal components;
b) nature of photoplethysmograph signal processing; and
c) sites of monitoring.

With reference to Table 1 as presented below, it is appreciated that although both AC and DC are affected by attenuating properties of the signal path (e.g., skin color), only DC is affected by background (i.e., absorption of relevant wavelengths by tissues within bone and muscle). AC is independent of background since it is the difference between peak and trough for a given beat, both of which have the same background component.

TABLE 1

| Factors Confounding AC and DC Measurements | | |
|---|---|---|
| | AC | DC |
| Attenuation | YES* | YES |
| Background | NO | YES |

*AC represents change in voltage: Peak—Baseline, each of which has the same background component. Hence, background is subtracted out of the AC measurement.

In developing the present invention, it has been appreciated that prior failures to identify or fully appreciate the changes in the vasculature at sites of photoplethysmograph monitoring have been attributable, in part, to auto-centering and dynamic recalibration of the photoplethysmograph signal, in an attempt to provide a stable "pleasant" waveform. However, these actions may obscure the impact of relevant physiologic changes. The lower channel of FIG. 1 shows a raw: plethysmographic tracing that has not been subjected to auto-centering and dynamic recalibration. Except when otherwise started, such a device is used for plethysmographic data presented herein. It is shown on an interfaced display after sampling at 200 Hz. Time is shown on the horizontal axis. Output in volts is shown on the vertical axis. With the onset of lower body negative pressure, a model of simulated hypovolemeia used in volunteers, the decline in circulating volume was reflected by a decline in plethysmographic voltage. In contrast, the auto-centering and dynamic recalibration features of the commercial photoplethysmograph (upper tracing of FIG. 1) masked this decline as if an undesirable diversion, thereby maintaining a stable tracing. Clearly, the manufacturers (and users) of such devices have not placed much credence on the potential for the photoplethysmograph to provide meaningful measurements of volume.

It has also been appreciated in the development of the present invention that while the most common monitoring site (i.e., finger) is prone to sympathetically mediated vasoconstriction, the forehead (FH), ear and other central regions (e.g., nasal ala) are relatively immune to vasoconstriction due to physiologic and pharmacologic challenges. In accordance with the aforementioned observations, recent studies by our research team show that AC monitoring at the ear (AC@Ear) and systemic stroke volume determined by voltage clamping on the arm declined similarly—by 39.3% and 41.3%, respectively—between baseline and onset of lightheadedness during lower body negative pressure. Likewise, AC monitoring at the Forehead (AC@FH) and echocardiographic measurement of stroke volume decreased by 26.5±11.8% and 26.8±9.6%, respectively (P=NS (P value non-significant)), after withdrawal of 2 units of blood from six healthy volunteers. In resting volunteers, intrasession (over the course of 30 min) and intersession (different days) consistencies of AC@FH readings were comparable to that reported for serial echocardiographic measures of stroke volume (related below).

As shown in FIG. 2, the aforementioned relationships have prompted the present introduction of the "AC Calibration Voltage." Except under rare exceptions (discussed below), "AC Calibration Voltage" is the AC voltage at the given site when the subject (and given site) is at rest ("$AC_{rest}$Voltage"). As used herein, $AC_{rest}$Voltage at the Forehead and Ear references the voltage change generated by the small portion of the stroke volume (which is generated by each heart beat) delivered to the given photoplethysmograph, more particular, it references voltage change generated by a small portion of a stroke volume delivered to a given noncentering, nonrecalibrating photoplethysmograph at a given site in a given subject under resting conditions. When attainable, $AC_{rest}$Voltage serves as the "Calibration Voltage," providing a basis for comparing all subsequent AC values for given photoplethysmograph at a given site as $AC_{rest}$Multiples (also referred to herein a $AC_{rest}$Mults(s) or number of $AC_{rest}$Mults). Unless otherwise specified, the $AC_{rest}$Voltage is used herein for calibration and hence $AC_{rest}$Mults are used as the unit for conversion of other voltages.

At any and all other time points, AC readings at the given site can be converted to $AC_{rest}$Mults, with the following equation (where # means "number of"):

# of $AC_{rest}$MULTS='GIVEN AC VOLTAGE'×'1 $AC_{rest}$MULT/$AC_{rest}$VOLTAGE', wherein $AC_{rest}$Voltage is the $AC_{rest}$Calibration Voltage as discussed above and 1 $AC_{rest}$MULT is equal to "1" for the purposes of calculation given that a single $AC_{rest}$MULT is characterized to equal the $AC_{rest}$Voltage.

Likewise, DC voltage values also are to be expressed as $AC_{rest}$Mults:

# of $AC_{rest}$MULTS='GIVEN DC VOLTAGE'×'1 $AC_{rest}$MULT/$AC_{rest}$VOLTAGE'

The number of $AC_{rest}$Mults can similarly be obtained with the following abbreviated equations:

# of $AC_{rest}$MULTS=GIVEN AC VOLTAGE/$AC_{rest}$VOLTAGE; and # of $DC_{rest}$MULTS=GIVEN DC VOLTAGE/$AC_{rest}$VOLTAGE.

The exception alluded to above occurs when the $AC_{rest}$Voltage does not constitute the calibrating voltage. This would be case if the first measurement on a subject (e.g., patient) is obtained after a challenge (e.g., insult such as surgery or an injury causing blood loss) has occurred before any measurements have been taken. At this time, the AC Calibration Voltage is more aptly termed $AC_{GivenTimePoint}$ Voltage and the AC Multiples are $AC_{GivenTimePoint}$Mults. Additionally, and as detailed below, since the present invention will allow measurements of blood volume, one may wish to calibrate vs. a less readily available technique such as the stroke volume measurements of echocardiography (if it is available). This typically would occur at rest ($SV_{rest}$). However, it may not have been sought during rest and thus may be obtained at a different time point and the calibration voltage would not be at rest. This is explored in greater detail in the context of volume measurements as discussed below.

The difficulties pertaining to obtaining an $AC_{rest}$ measurement often may be avoidable. Healthcare providers, military personnel and others facing potential blood loss should be assured by documentation that $AC_{rest}$ has high intrasession and intersession stability. Its consistency was comparable to that reported for the echocardiography, the "gold standard." In recently obtained photoplethysmographic data obtained over multiple sessions, 2× standard error of $AC_{rest}$Voltage averaged 8% of mean; this was less the 11% for SV that was reported using echocardiography on successive days (Ihlen H, et l Amer J Cardiol 1987; 115:59(9) 9756). Moreover, intrasession 2×SE/Mean averaged only 3%. The consistency of $AC_{rest}$Voltage means that it can be recorded prior to the start of surgery or even days, weeks, months . . . prior to going into battle.

It is anticipated that reliability and consistency can be improved by use of artifact and movement rejection algorithms and multiple filters to enable delineation of blood vs. other tissues and ideally isolate the arterial and venous blood components. Substrate concentrations and arterial/venous differences thereof also may be assessed.

Each of the above equations facilitates AC and DC comparison and offers the added benefit of removing the impact of attenuation, since each AC and DC measurement and the calibrating $AC_{rest}$Voltage are attenuated proportionately. The stability of $AC_{rest}$ values at the Ear and Forehead under resting conditions bolsters the foundation for the present introduction of $AC_{rest}$Mults during local and systemic challenges in two sets of healthy volunteers.

More particularly, and with reference to FIG. 2, the introduction of $AC_{rest}$Mults to eliminate impacts of attenuation and inter-device differences within and among subjects is achieved in the following manner. In accordance with the present method and system, if AC is isolated by high pass (e.g., >0.5 Hz) filtering, a preferred embodiment entails establishing $AC_{rest}$Voltage$_{(filtered)}$ as equaling the mean AC height of a selected section of a filtered tracing at rest. If alternatively AC is determined as peak-to-trough difference of individual pulses, a preferred embodiment entails establishing $AC_{rest}$Voltage$_{(peak\ analysis)}$ as equaling the height of single beat or mean height of multiple beats at rest; alternatively, it may be calculated as by dividing beat area by beat width. For purposes of overall consistency, it will be advisable to have universal consensus as to a consistent means of $AC_{rest}$Voltage measurement. Since the differences are relatively small (and a consensus has not yet been reached), the methods are used interchangeably herein.

Regardless of whether AC is isolated by high pass filtering or AC is determined as peak-to-trough difference, any and all photoplethysmographic voltages are converted to the number of $AC_{rest}$Mults, as per the equations cited above.

Figure 14:
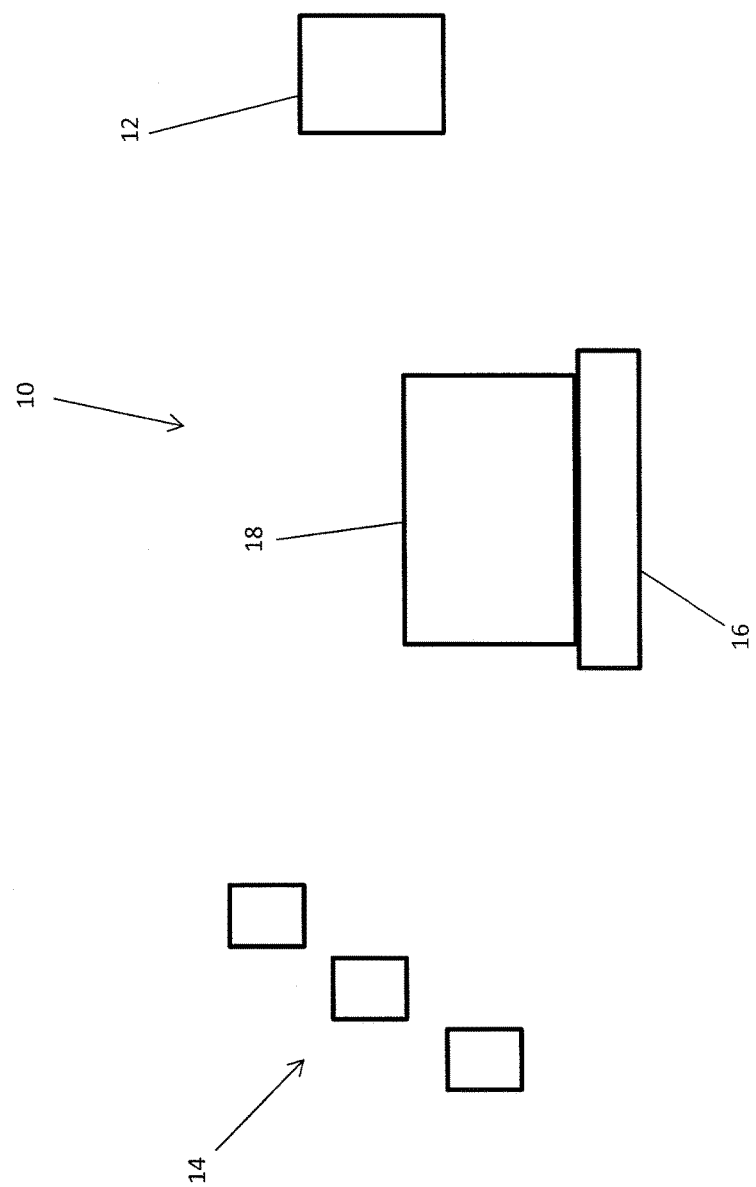
FIG. 14 is a schematic of a system in accordance with the present invention.

One can also define changes in AC ($\Delta$AC) or changes in DC ($\Delta$DC) in terms of $AC_{rest}$Mults. For example, For AC:

$\Delta$AC='#$AC_{rest}$MULTS for $AC_{NEW}$'-'#$AC_{rest}$MULTS for $AC_{PRE}$'; or $\Delta AC = \Delta AC\ VOLTAGE \times `1\ AC_{rest}MULT/AC_{rest}\ VOLTAGE`$ For DC $\Delta DC = `\#AC_{rest}MULTS\ for\ DC_{NEW}` - `\#AC_{rest}MULTS\ for\ DC_{PRE}`$; or $\Delta DC = \Delta DC\ VOLTAGE \times `1\ AC_{rest}MULT/AC_{rest}\ VOLTAGE`$ As those skilled in the art will certainly appreciate, and with reference to FIG. 14, the methodology described above is preferably implemented via a computer based system 10 linked to a conventional photoplethysmograph 12 and a variety of data source(s) 14 as may be deemed necessary, which cumulatively represent a database of information. The system 10 is further provided with output displays and input mechanisms (for example, computer stations 16 with a graphical user interface 18) as are well known in the art. It is further appreciated, the various components making up the present system may be integrated into a single station from which information is input, processed and output. Similarly, the present system may be configured in more elaborate arrangements with multiple data sources, input mechanisms and output displays, or it may be a standalone unit. Items such as demographic data may be hand-entered. Options may be available for channel selection, time and output parameters, with split screens to allow comparison among sections of data. Data may be processed for comparison within and among parameters, within and among monitoring devices.

Objectives & Hypotheses of Study Models:

With the foregoing introduction of $AC_{rest}Mults$ in mind, the objective and hypotheses underlying the present invention where tested on first and second series of subjects. The local challenge ($1^{st}$ series of subjects) entailed photoplethysmograph monitoring during transdermal application of vasoactive agents [nitroglycerin (Nitro) and nicotine (NIC)] as translucent "micro-patches," an expansion of prior work where laser Doppler flowmetry confirmed that transdermal nitroglycerin and acetylcholine cause local increases in flow, but could not distinguish arterial and venous responses. The use of such micro-patches is disclosed in U.S. patent application Ser. No. 12/059,383, entitled ""MICRO-PATCH" FOR ASSESSMENT OF THE LOCAL MICROVASCULATURE AND MICROCIRCULATORY VASOREACTIVITY," filed Mar. 31, 2008, which is incorporated herein by reference. In accordance with the present invention, the hypotheses that was tested:

1a) Increases (↑) in AC and DC would differ significantly within each study agent;

1b) ↑DC/↑AC would differ significantly between the two study agents (consistent with their different pharmacologic activities); and 1c) The relationships between DC and AC at the Forehead would not differ significantly from literature reports of systemic volumes and changes thereof.

Such would suggest that the inventive embodiments can transform photoplethysmographic values at a central site such as the Forehead or Ear into a window that enables viewing the local microcirculation as a microcosm of the systemic circulation and its relative arterial and venous volumes.

The systemic challenge ($2^{nd}$ series) entailed sequestration of up to 1,500 ml blood in the lower extremities by progressive application of lower body negative pressure (LBNP), wherein it has been shown that ↓AC at a central site (Ear, Forehead) is comparable to ↓SV (measured in the periphery by voltage clamping), but assessments of venous volume and overall volume heretofore have not been achieved. It is hypothesized that 2a) The LBNP-induced ↓DC (in $AC_{rest}Mults$) would correspond to the relative LBNP-induced "loss" of volume reported with this challenge;

2b) By linking AC to a measured (or estimated) systemic stroke volume ($SV_{rest}Volume$), we would be able, for the first time, to use the photoplethysmograph to quantify blood loss and blood replacement and, more specifically, to distinguish the arterial and venous components;

2c) Increases in AC and DC during recovery (upon release of negative pressure) would demonstrate a Frank Starling-like relationship with respect to the relationship of venous and arterial blood (as measured herein by photoplethsymography); and 2d) Comparative changes in DC and AC at finger and Ear would be consistent with homeostatic responses to blood loss (regional vasoconstriction, mobilization of blood from storage sites).

$1^{st}$ Series of Subjects: Local Interventions 10 healthy non-smoking volunteers were recruited and written informed consent was obtained. Each subject lay supine on a bed in a temperature regulated ~22° C. room. The Forehead was gently wiped with wet gauze and patted dry. Then, one of two drug "micro-patches" was prepared (based on randomized drug assignment to the first or second session (one hour apart). A nitroglycerin micro-patch was prepared by cutting a 1×1 cm section from a transparent commercial patch of standard concentration (Minitran, 3M Pharmaceuticals, Northridge, Calif.). A nicotine micro-patch was similarly prepared by cutting a 1×1 cm section from a transparent commercial patch of standard concentration (Nicoderm CQ, GlaxoSmithKline). The agents were selected because of their different modes of action (nitroglycerin being a nitric oxide donor at vascular endothelium, nicotine being a neurotransmitter at accessible pre-to-post ganglionic junctions) and their FDA-approved clinical availability as transparent transdermal patches. Each was available in a single concentration; hence equipotent doses were not sought in this initial investigation; however, comparisons of multiple doses of multiple drugs certainly could be achieved with the present invention.

In accordance with the randomized selection, the nitroglycerin or nicotine micro-patch was placed on the study site and promptly covered with an nonautocentering, nonrecalibrating reflectance photoplethysmograph interfaced via bridge amplifier to a data acquisition system (PowerLab, ADInstruments, Boulder Colo.) for sampling at 200 Hz for continuous recording with customized commercially available software (Chart 7.0, ADInstruments). A second photoplethysmograph was concurrently placed on contralateral forehead for control readings and subsequent zeroing. After a period of stabilization (~10 sec), baseline ("pre") readings were obtained. Ten minutes later (after attainment of micro-patch-induced plateau) "drug" measurements were recorded. As shown in FIG. 2, the raw signal was separated in AC and DC components by respectively applying high pass (>0.5 Hz) and low pass (<0.5 Hz) filters. (Other filters, such as band pass or notch filters, can similarly be employed so long as the same filtering window is used for all such monitoring within the given subject). The raw, AC and DC signals were exported to a spreadsheet; and $AC_{pre}$, $AC_{drug}$, $DC_{pre}$, and $DC_{drug}$ were determined from 10 second segments during "pre" and "drug" for each agent. $AC_{pre}$ and $DC_{pre}$ were recorded as the respective 10 second averages.

$AC_{drug}$ and $DC_{drug}$ were recorded for 10 sec after attainment of a plateau (at approximately 10 min). In accordance with this invention, other intervals, including single beats, can be used.

To facilitate comparison between AC and DC and the relative impacts of nitroglycerin and nicotine within and among subjects, all data were converted as per the embodiment(s) of the present invention shown in FIG. 2 to $AC_{rest}$ Mults by normalizing each value to the $AC_{rest}$ Voltage (which was the same as the AC Calibration Voltage and the undisturbed $AC_{pre}$ value). For each successive reading, the # of $AC_{rest}$Mults was determined as per the description of FIG. 2 above.

$AC_{drug}$ as # of $AC_{rest}$MULTS='GIVEN $AC_{drug}$ VOLTAGE'×'1 $AC_{rest}$MULT/ $AC_{rest}$VOLTAGE'→GIVEN $AC_{drug}$VOLTAGE/ $AC_{rest}$VOLTAGE $DC_{drug}$ as # of $AC_{rest}$MULTS='GIVEN $DC_{drug}$ VOLTAGE'×'1 $AC_{rest}$MULT/ $AC_{rest}$VOLTAGE'→GIVEN $DC_{drug}$VOLTAGE/ $AC_{rest}$VOLTAGE Conversion to $AC_{rest}$Mults enabled comparisons of $\Delta AC$ and $\Delta DC$ within and among drugs, within and among subjects. This was not attainable with monitors that solely focus on either the arterial (e.g. arterial blood pressure monitors) or venous (central venous pressure monitors) measurements or even with plethysmographic algorithms that perform contour analysis (since this is limited to the AC component). The inventive conversion to $AC_{rest}$Mults also enabled testing the hypothesis that ↑DC/↑AC ratio would be greater in response to nicotine than nitroglycerin. Since it is a direct nitric oxide donor, nitroglycerin would impact the vascular endothelium of all penetrable vessels beneath the micro-patch. Alternatively, the primary sites of action for nicotine would be nicotinic pre-/post-ganglionic receptors of the autonomic nervous system, of which only parasympathetic fibers synapse at the end organ; hence, nicotine should predominantly affect volume downstream of the innervated precapillary sphincter and hence spare more proximal arteries and meta-arterioles. This would constitute a vital means to assess local microcirculatory pharmacology and provide into systemic microcirculatory pharmacology in accordance with U.S. patent application Ser. No. 12/059,383, entitled "'MICRO-PATCH'" FOR ASSESSMENT OF THE LOCAL MICROVASCULATURE AND MICROCIRCULATORY VASOREACTIVITY,"

Drug impacts on pulsatile (~arteriolar capillary) and non-pulsatile (~venular) segments of the underlying microvasculature were further assessed by calculating changes in compliance as per the methodology outlined in FIG. 3. Respective compliance changes were determined by dividing $\Delta AC$ and $\Delta DC$ (in $AC_{rest}$Mults) by 65 mmHg and 17.5 mmHg, consensus pressures at distal arterioles and venules (Best et al 1966, Intaglietta et al 1970). Since the numerator was a voltage-based measurement (not actual volume), the photoplethysmograph generated "ACcompliance" and "DCcompliance" values are expressed in "$AC_{rest}$Mults/mmHg" units (herein introduced).

Table 2, below, summarizes the drug-induced changes in AC in terms of raw voltage as well as $AC_{rest}$Mults (wherein $AC_{pre}$ constituted the $AC_{rest}$ reading). Without such normalization (conversion to $AC_{rest}$Mults), $AC_{pre}$ readings at the control site ranged from 0.0012 volts in our darkest to 0.0181 volts in our lightest subject—the wide range would complicate intersubject comparisons of drug effect. In accordance with the invention, the impact of attenuation on DC as well as AC was eliminated by normalizing to $AC_{rest}$. The mean raw AC values (volts) increased from $AC_{pre}$=0.0124 to $AC_{Nitro}$=0.0285 (p=0.0005) and $AC_{pre}$=0.0101 to $AC_{NIC}$=0.0291 (p=0.0001). Establishing $AC_{pre}$ as the $AC_{rest}$ Voltage=1 $AC_{rest}$Mult converted the $AC_{pre}$ and $AC_{drug}$ values to 1 and 2.55 $AC_{rest}$Mults for nitroglycerin and to 1 to 3.01 $AC_{rest}$Mults for nicotine. These amounted to relative increases (% ↑) of 155% and 201%, respectively. Dividing $\Delta AC$ by 65 mmHg provided absolute increases in AC compliance of 0.0248 $AC_{rest}$Mults/mmHg and 0.031 $AC_{rest}$Mults/mmHg for the two agents.

TABLE 2

| Photoplehysmo- graphic Values | Affected by Attenuation? | Affected by Background? | AC | |
|---|---|---|---|---|
| | | | Nitro Mean ± SD | NIC Mean ± SD |
| Raw AC Values in volts: | | | | |
| $AC_{pre}$ | YES | No | 0.0124 ± 0.008 | 0.010 ± 0.01 |
| $AC_{drug}$ | YES | No | 0.0285 ± 0.016 | 0.029 ± 0.01 |
| $\Delta AC$ | YES | No | 0.0161 ± 0.011 | 0.019 ± 0.01 |
| AC Voltages Converted to $AC_{rest}$Mults (obtained by normalizing to voltage of ACpre): | | | | |
| $AC_{pre}$ (in $AC_{rest}$Mults) | No | No | 1 | 1 |
| $AC_{drug}$ (in $AC_{rest}$Mults) | No | No | 2.553 ± 0.946 | 3.01 ± 0.971 |
| $\Delta AC$ (in $AC_{rest}$Mults) | No | No | 1.558 ± 0.946 | 2.01 ± 0.97 |
| AC in $AC_{rest}$Mults Converted to ACcompliance (in $AC_{rest}$Mults/mmHg): | | | | |
| $\Delta AC_{rest}$Mult compliance (in $AC_{rest}$Mults/mmHg) | No | No | 0.0239 ± 0.025 | 0.0309 ± 0.024 |

Likewise, Table 3 summarizes the drug-induced changes in DC in raw values as well as $AC_{rest}$Mults. The DC raw values (volts) increased from $DC_{pre}$=1.82 to $DC_{Nitro}$=1.93 and from $DC_{pre}$=1.41 to $DC_{NIC}$=1.68. Having established $AC_{pre}$ as the $AC_{rest}$Voltage, the voltages converted to $DC_{pre}$ and $DC_{drug}$ values of 208.27 and 222.31 $AC_{rest}$Mults for nitroglycerin and to 175.22 and 204.77 $AC_{rest}$Mults for nicotine. Hence DC increased by 14.04±10.2 and 29.56±27.7 $AC_{rest}$Mults for nitroglycerin and nicotine respectively. This amounted to respective % ↑DC of 6.42%% and 23.41%, spuriously low because DC readings included background, which impacted the denominator ($DC_{pre}$) but not $\Delta DC$ (addressed below). Next, $\Delta$Compliance was determined by dividing $\Delta DC$ by 17.5 mmHg. This provided ↑DC compliance of 0.80 $AC_{rest}$Mults/mmHg and 1.69 $AC_{rest}$Mults/mmHg for the two agents; in light of distorting impact of background on the denominator, % ↑DCcompliance was not calculated.

The $\Delta DC/\Delta AC$ ratios were 7.31±8.2 and 14.23±4.49 for nitroglycerin and nicotine, respectively (p=0.015 by one-tailed paired test for inter-drug differences), indicating that nicotine caused a significantly greater preponderance of DC (i.e., venous) dilation. The respective ↑DCcompliance/ ↑ACcompliance ratios were 33.56 and 54.57 for nitroglycerin and nicotine (p=0.046 for the greater ratio after nicotine).

TABLE 3

| Photo-plethysmographic Values | Affected by Attenuation? | Affected by Background? | DC Nitro Mean ± SD | DC NIC Mean ± SD |
|---|---|---|---|---|
| $DC_{pre}$ | YES | YES | 1.824 ± 0.39 | 1.413 ± 0.54 |
| $DC_{drug}$ | YES | YES | 1.929 ± 0.35 | 1.676 ± 0.47 |
| $\Delta DC$ | YES | No | 0.11 ± 0.07 | 0.26 ± 0.14 |
| $DC_{pre}$ (in $AC_{rest}$Mults) | No | YES | 208.270 ± 128.28 | 175.22 ± 102.99 |
| $DC_{drug}$ (in $AC_{rest}$Mults) | No | YES | 222.3106 ± 138.471 | 204.77 ± 104.66 |
| $\Delta DC$ (in $AC_{rest}$Mults) | No | No | 14.0404 ± 14.87 | 29.56 ± 17.85 |
| $\Delta DC$ Compliance (in $AC_{rest}$Mults/mmHg)) | YES | No | 0.8023 ± 0.850 | 1.689 ± 1.02 |

Oft-cited reports in the literature that nitroglycerin caused a % ↑in venous compliance that was ~1.8 times the % ↑increase in arterial compliance (Imhof 1980, Mackenzie 1977) provided the opportunity for testing whether photoplethysmograph monitoring of nitroglycerin micro-patch impact on the local microvasculature paralleled invasive assessments of intravascular nitroglycerin administration into systemic vessels that led to the designation of nitroglycerin as primarily a venodilator. However, to test whether the relative micro-patch induced changes were similar to the relative venous/relative arterial changes (% ↑venous/% ↑arterial) measured systemically, it was necessary to convert absolute measures of Δcompliance to measures of Δcompliance relative to prenitroglycerin measurements. The % ↑AC and % ↑ACcompliance were readily determined: the use of $AC_{rest}$Mults eliminated the impact of attenuation and AC is, in and of itself, independent of background. Conversely, the % ↑DC and % ↑DCcompliance were not readily determinable: the ↑$DC_{Nitro}/DC_{pre}$ ratio was confounded by the predominant impact of background.

Figure 4:
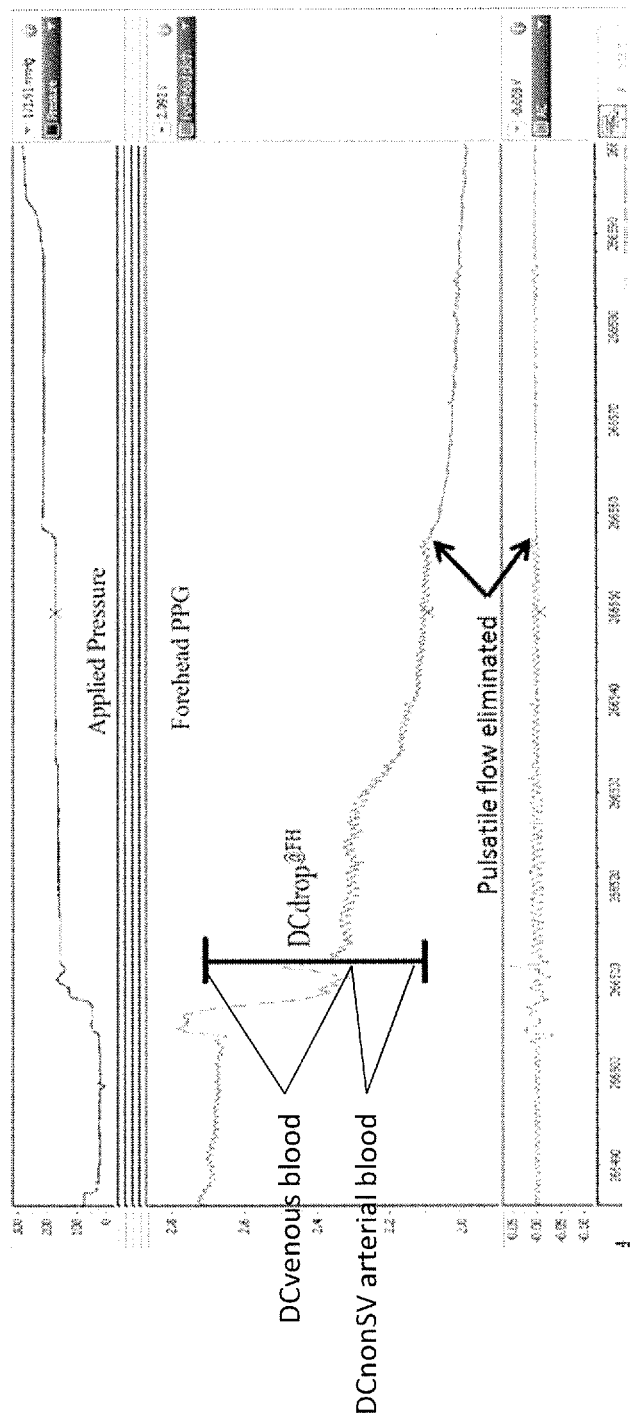
FIG. 4 is a graph of a plethysmographic signal showing means for isolation of DCblood from DCbackground and further distinguishing the former into $DCblood_{venous}$ and $DCblood_{nonSV\ arterial}$ in accordance with the present invention.

The present method and system address this with mechanisms to isolate what is herein termed "DCblood" from "DCbackground" (FIGS. 4-6); prior to the present invention, these were assumed to be inseparable components of the phtoplethysmogaphic signal. A mechanism for isolating the DCblood component from the DCbackground component was therefore introduced. As shown in FIG. 4, in the final six subjects, increasing pressure was applied to the photoplethysmograph at the untreated control site. Application of slowly increasing pressure caused progressive displacement of capillary, venous, arteriole and arterial blood to the point that vascular volume no longer contributed to the photoplethysmograph signal.

The progressive application of pressure to eliminate blood beneath the photoplethysmograph was chronicled via a pressure transducer mounted atop the photoplethysmograph sensor (top panel of FIG. 4). Progressive decline in the plethysmograph are shown for the raw photoplethysmograph signal (middle panel) and AC component (isolated in bottom panel with a 0.5 to 3.0 Hz digital band pass filter). The drop in voltage until loss of the pulsatile signal represented the DCblood component. The remaining voltage represented background. It also can be seen in FIG. 4, the DCblood is really a composite of what I herein introduce as $DCblood_{venous}$ and $DCblood_{nonSV\ arterial}$. $DCblood_{venous}$ is the blood that is eliminated beneath photoplethysmograph by applied pressure that is not sufficient to compress arteries and arterioles (as shown by persistence of pulsatie signal in bottom channel of FIG. 4). $DCblood_{nonSV\ arterial}$ is shown by volume that is displaced between the initial displacement of venous blood and the ablation of the pulsatile signal. The last component to be ablated is generated by the pulsatile delivery of the SV (AC component of photoplethysmograph). The signal which remains is DCbackground, the contribution to the signal by nonblood tissues. These different parameters have different uses: comparison of AC and $DCblood_{venous}$ is applicable to a setting such as the present comparison of arterial and venous impacts of a vasoactive medication. Changes in systemic volume, as per the model of simulated blood loss (lower body negative pressure) described below, may best be assessed by SV and DCblood (i.e, $DCblood_{venous}+DCblood_{nonSV\ arterial}$).

Figure 5:
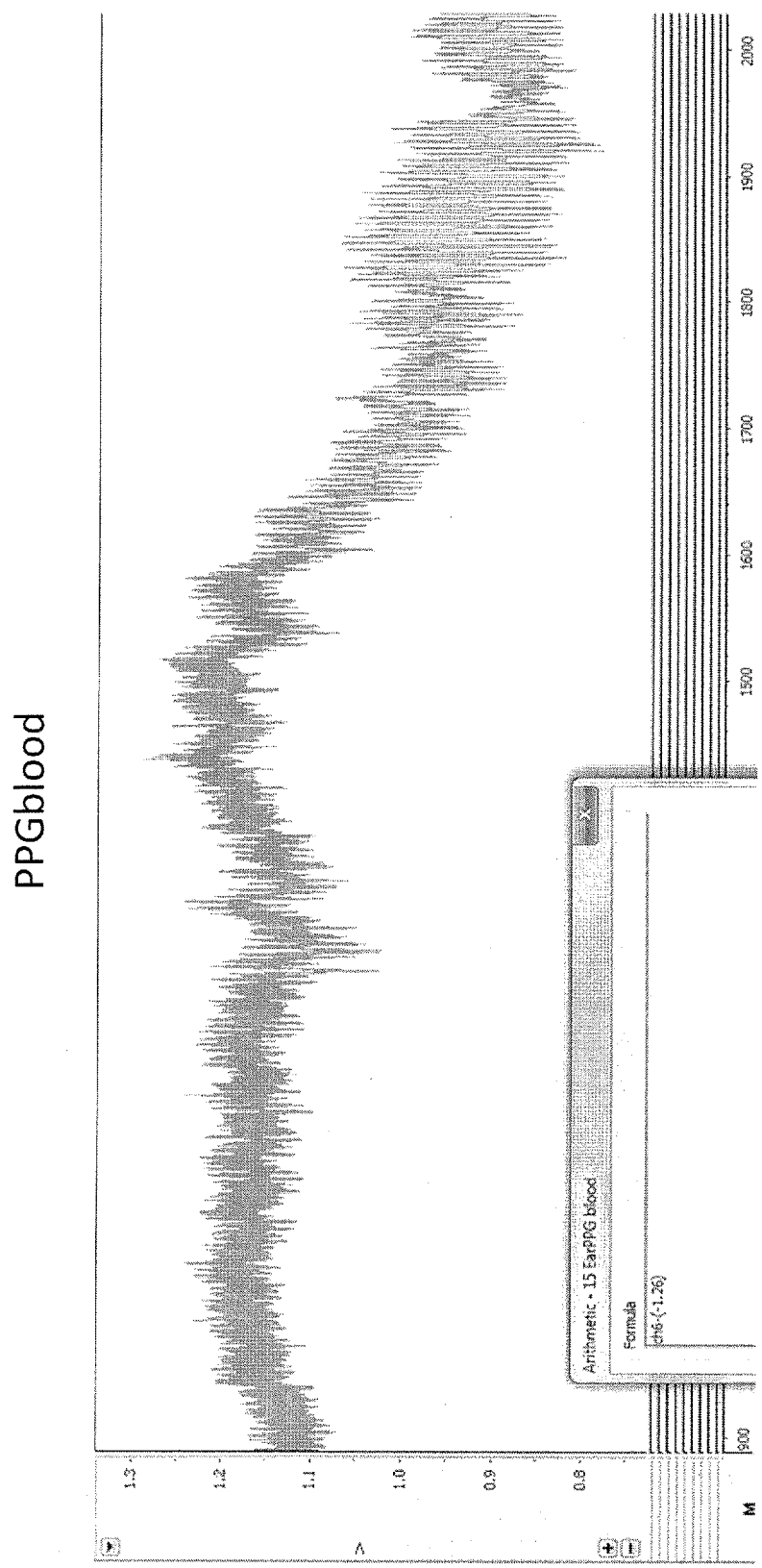
FIG. 5 shows the signal from the lower panel of FIG. 1 with the DCbackground component subtracted such that PPGblood (DCblood+SV) is graphed. Portions of baseline and challenge segments in a subject undergoing lower body negative pressure (LBNP). This shows channel 15 (of a ≤36-channel acquisition system), the tracing of Ear from which ~DCbackground has been subtracted so that DC now represents only blood (DCblood) and the given channel shows PPGblood. This was achieved as follows: during @rest period prior to LBNP, each beat was identified using a peak analysis program and then calculated mean AC@rest (0.035 volts in this subject) and mean DC at rest (~0.126 volts). 32×ACrestVoltage (→1.134 volts) was subtracted from mean DC, since trials such as that shown in FIG. 4 indicate that DCblood (DCblood$_{venous}$+DCblood$_{nonSvarterial}$) averages 32.4 (i.e., approximately 32 times AC$_{rest}$Voltage). The difference approximated mean background (~−1.26 volts). −1.26 volts was then subtracted from each value in the raw signal to generate the current "blood" signal. Note that the background was a negative number, as was the raw signal shown in the bottom panel of FIG. 1, an example of the difficulty interpreting the raw voltage provided by the photoplethysmograph.

The voltage decline associated with loss of all pulsations is defined as $DCblood_{rest}$. This was quantified in $AC_{rest}$Mults, wherein $AC_{pre}$ prior to the application of pressure was the $AC_{rest}$Voltage and $DCblood_{rest}$ is the drop caused by external pressure at an otherwise "resting" site. The remaining signal was DCbackground. In addition, as shown in FIG. 5, subtracting DCbackground from all photoplethysmograph readings enables continuous display of DCblood values (as opposed to only DCblood at the given time point (typically at rest). In essence, DC blood is equivalent to the blood component of the raw photoplethysmographic signal (PPG-blood) minus the contribution of the stroke volume (i.e., minus 1 $AC_{rest}$Mult).

In the present series of subjects, based on intersite similarity among forehead site similarities, the $DCblood_{rest}$ value in $AC_{rest}$Mults) determined at the control site was utilized as the $DCblood_{pre}$ value at the contralateral drug site (so as to avoid the need to press on and thereby disturb the drug site). When expressed as $AC_{rest}$Mults to facilitate intersubject comparison, $DCblood_{venous}$ averaged 25.6±18.4 $AC_{rest}$Mults. This value was independent of background (independence achieved by aforementioned zeroing) as well as attenuation (independence achieved by converting to $AC_{rest}$Mults). The remaining signal constituted DCbackground+$DCblood_{nonSV\ arterial}$; the latter, which was not the focus of our micropatch assessments, averaged 5 $AC_{rest}$Mults.

As related in FIG. 6, the introduction of DCblood enabled measurement of relative as well as absolute measures of DC and ΔDC as well as of DCcompliance and ΔDCcompliance; this integrates determination of $DCblood_{rest}$ with the embodiment(s) of FIGS. 2 and 3. Dividing ΔACcompliance by $AC_{pre}$ in $AC_{rest}$Mults and dividing ΔDCcompliance by $DCblood_{pre}$ in $AC_{rest}$Mults identified a % ↑DCcompliance/% ↑AC compliance (per $AC_{rest}$Mults) ratio that was 1.824±1.32 (p-0.009 by one-tailed paired t-test for AC vs DC difference) (Table 4). The 95% confidence interval ("CI") of 0.816 clearly encompassed the literature reports of a Δvenous/Δarterial compliance ratio=1.8.

TABLE 4

| Photoplethysmographic Values | AC | Traditional DC (=DCblood + DCbackground) | DCblood |
|---|---|---|---|
| Pre (in $AC_{rest}$Mults) | 1 | 228.036 ± 141.5 | 25.547 ± 18.37 |
| Δ Drug − Pre (in $AC_{rest}$Mults) | 1.822 ± 0.452 | 17.785 ± 16.51 | |
| Δ Drug − Pre (in $AC_{rest}$Mults/mmHg) (based on literature- | 0.0248 ± 0.02 | n/a | 1.016 ± 0.94 |

TABLE 4-continued

| Photoplethysmo- graphic Values | AC | Traditional DC (=DCblood + DCbackground) | DCblood |
|---|---|---|---|
| derived pressures of 65 mmHg and 17.5 mmHg for AC and DC vascular beds, respectively) | | | |
| ΔCompliance/ Pre | .0248 ± 0.017 | n/a | 0.048 ± 0.0494 |

It should be noted that related applications in the spirit of the present invention include utilizing the pressures required for eliminations of $DCblood_{venous}$ and $DCblood_{nonSVarterial}$ as a pressure components of measures of compliance. It also should be noted that drugs and doses are not limited to those employed above. For example, application of eutectic mixture of local anesthetic (EMLA) generated a ↑DC/↑AC ratio of 13.6. This is consistent with it being a dilator of smooth muscle and thus more likely to have a relatively larger impact on AC than nitroclycerin or nicotine.

Description of Additional Embodiments

Figure 7:
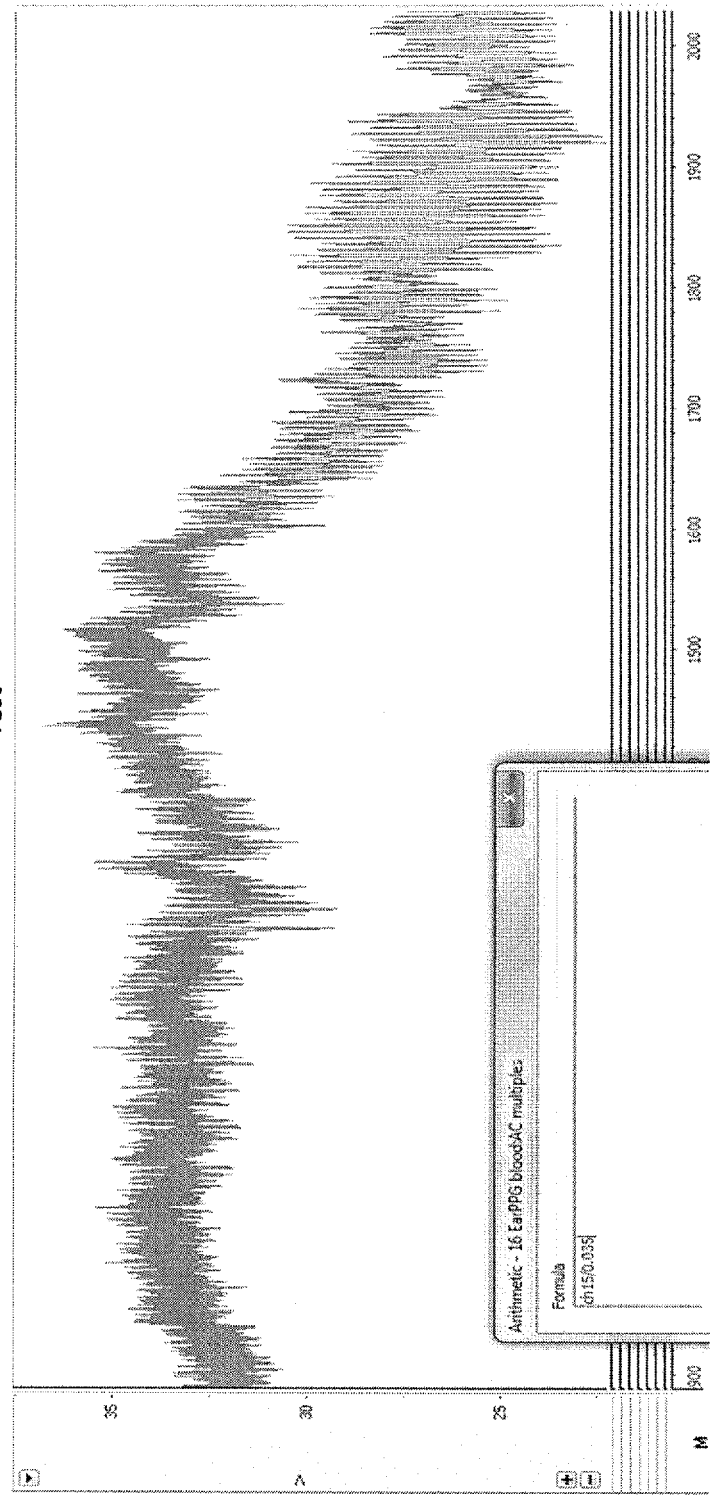
FIG. 7 shows how, using embodiments of the present invention, the continuous DCblood signal is converted from a graph of voltages to a graph of AC$_{rest}$Mults. Tracing (channel 16 of ear plethysmograph) displays continuous plethysmographic signal with background subtracted (PPGblood of FIG. 5) in terms of AC$_{rest}$Mults. As stated with respect to FIG. 5, in the present subject, DCblood$_{pre}$ (prior to the onset of LBNP) was equivalent to 32.4 AC$_{rest}$Mults. Alternatively DCblood@rest can be measured by applying external pressure at given site as per FIG. 4).
Figure 8:
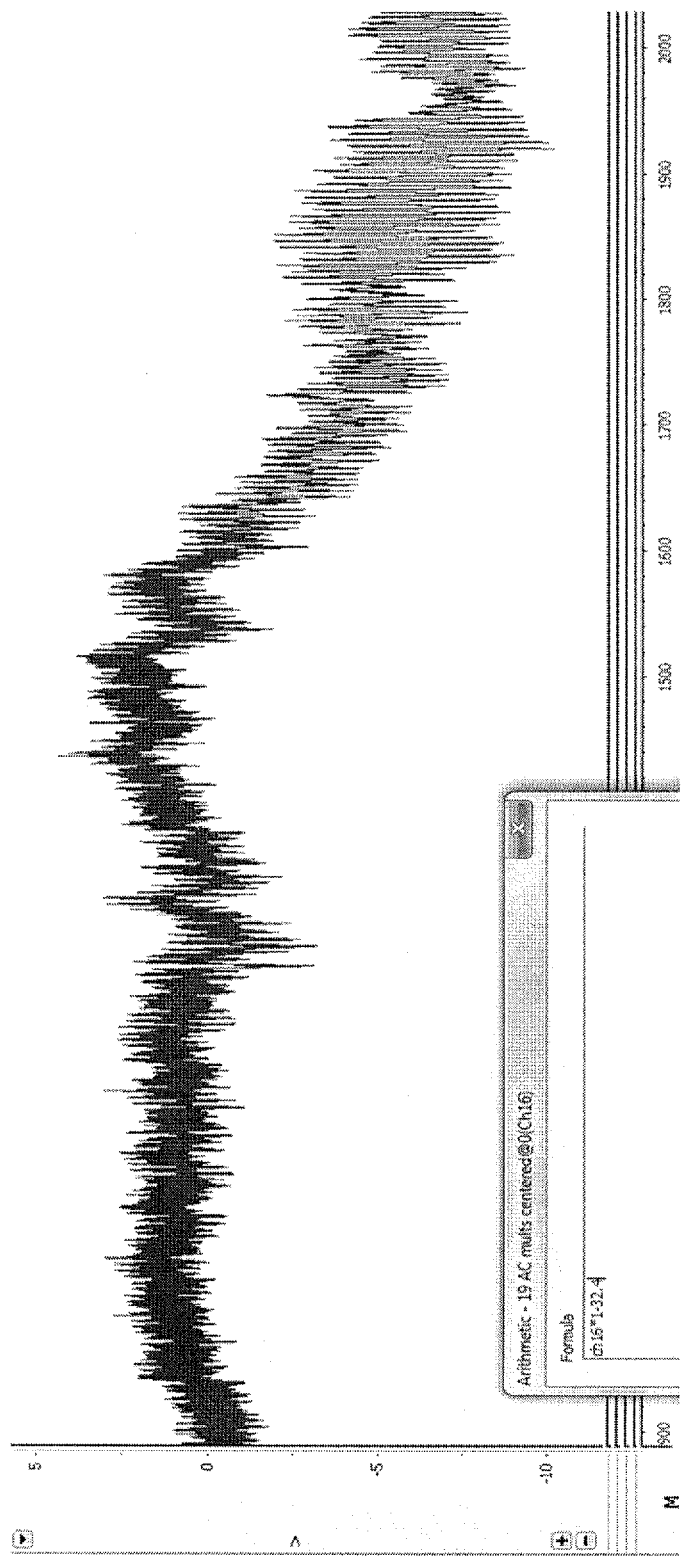
FIG. 8 shows the tracing of FIG. 7 with an offset so that baseline is centered at 0. Tracing (channel 19) where Ear plethysmograph tracing, already with background subtracted and already converted to AC$_{rest}$Mults for channel 16 is now being centered at 0 AC units. To achieve this, the mean of PPGblood values were first calculated during the preLBNP period (in AC units); the calculation provided a mean value of 32.4 units. The desired y-intercept of "0" is achieved by solving for 'b' with equation 0=(1)×(32.4)+b; b is found to be −32.4. I then generated continuous graph shown here with the equation 0=(1)×(channel 16 serial values)+(−32.4).
Figure 9:
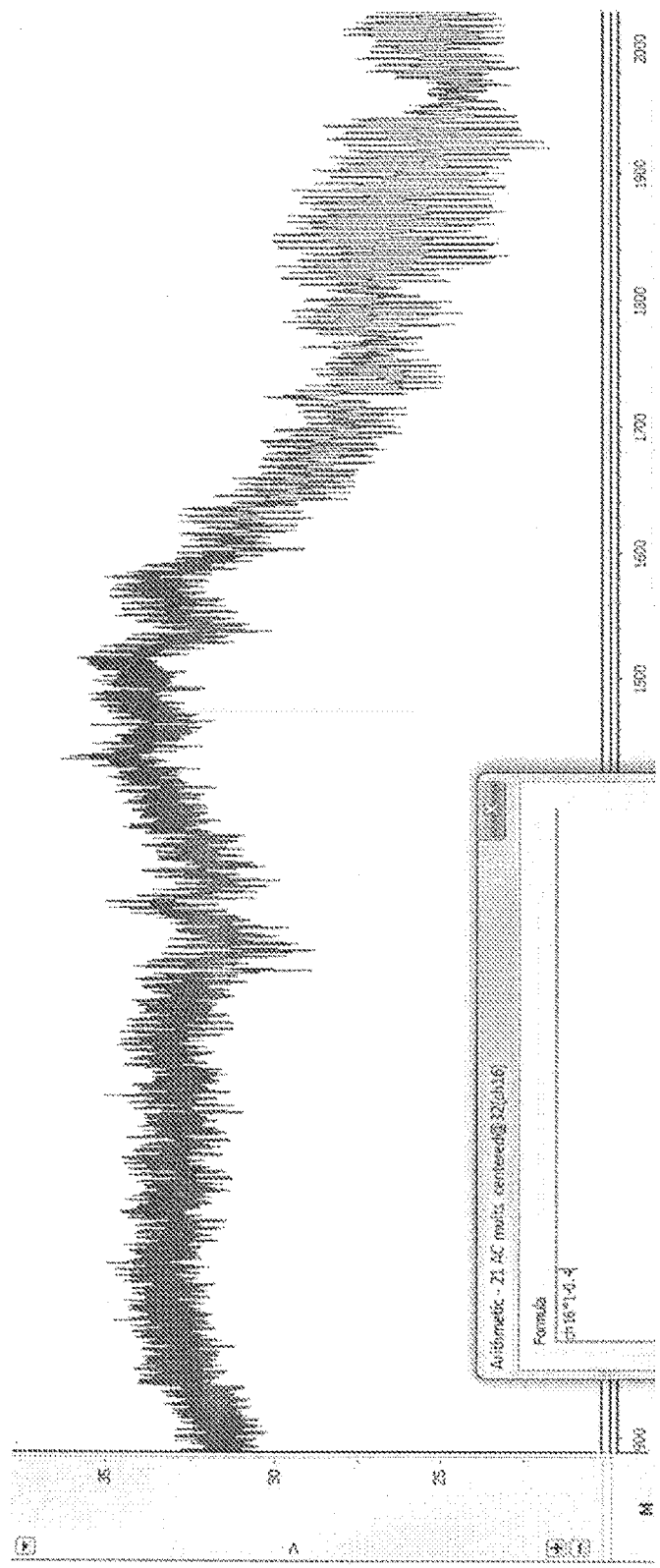
FIG. 9 shows the tracing of FIGS. 7 and 8, centered at 32 on the y-axis, a value that is amenable to consistent display among patients, since resting volume in healthy subjects is ~32 AC$_{rest}$Mults. Tracing (Channel 21) shows centering of y-axis at ~32 AC$_{rest}$Mults, thereby approximating combined DCblood$_{venous}$+DC DCblood$_{nonSvarterial}$volume. Data generated from ch 16, 32=(1)(32.4)+b; producing b=−0.4. Graph equation for given y intercept=32: (1)×(Ch16)−0.4.

FIGS. 7-9 show the impact of embodiments of the present invention on photoplethysmographic waveforms and their AC and DC components. In many of such applications, the conversion is inherently obvious (i.e., simply based on conversion of voltage to $AC_{rest}Mults$). However, especially as one seeks uniform axes for display (as enabled by inventive conversion to uniform units), it is preferred to rely on an equation for determining variables and subsequent graphing. This integrates inventive embodiments as components of the equation for a straight line. For example, establishment of a means for consistent display of photoplethysmographic data within and among subjects can be achieved with an inventive conversion factor and determination of the desired value of y-axis crossing in $AC_{rest}Mults$ (Table 5).

four channels as may be recorded simultaneously during a lower body negative pressure challenge (or subsequently created from an existing channel during post-collection processing). The initial baseline (preLBNP) section is to the left. Then, as shown by the dotted lines, lower body negative pressure was applied to as low as −60 mmHg. Then, at a little after 30 minutes, the pressure was released, and the recovery phase was entered. (The details of the lower body negative pressure challenge will be described below).

For each of the channels, the left-hand vertical axis represents the magnitude of the signal. The horizontal axis represents time (25:00 to 34:30 minutes). As can be seen by the series of horizontal lines running between the first and second channels, up to 16 channels were recorded during the study, but only four are shown herein. All represented data are from nonautocentering photoplethysmographs.

The second channel (labeled 14) has isolated the AC signal via high pass filter. As expected, the magnitude of the AC signal decreased with progressive lower body negative pressure and then rebounded upon release of the negative pressure. The third channel (labeled 15) has converted the raw voltage of first channel 6 to $AC_{rest}Mults$ as may be accomplished by dividing the voltage of each data point ($AC_{GivenTimePoint}Voltage$) by the $AC_{rest}Voltage$. The fourth channel (labeled 16) shows the continuous $AC_{rest}Mults$ after the pre-LBNP mean (in volts) has been subtracted from the signal.

Figure 10:
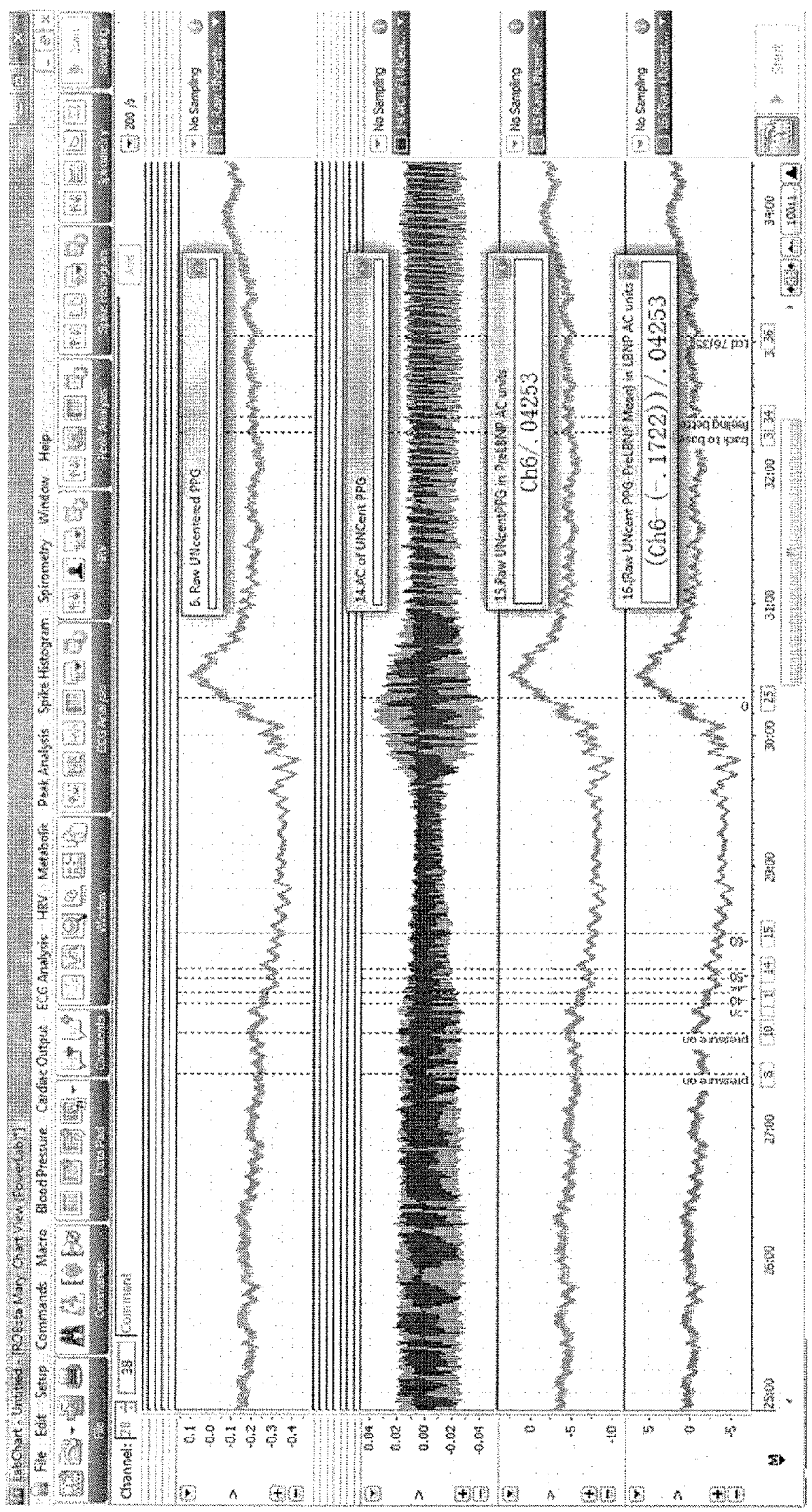
FIG. 10 is a screen shot of a multichannel data acquisition system, showing four channels that have been adapted to show multiple synchronous configurations of the same signal from an ear photoplethysmograph. From top to bottom channel 6=continuous raw signal during segment during application of and recovery from lower body negative pressure: 14=AC component 15=signal converted to AC$_{rest}$Mults, 16=signal in AC Mults shifted so that period prior to recovery is centered at 0 by adding difference from preLBNP mean.
Figure 11:
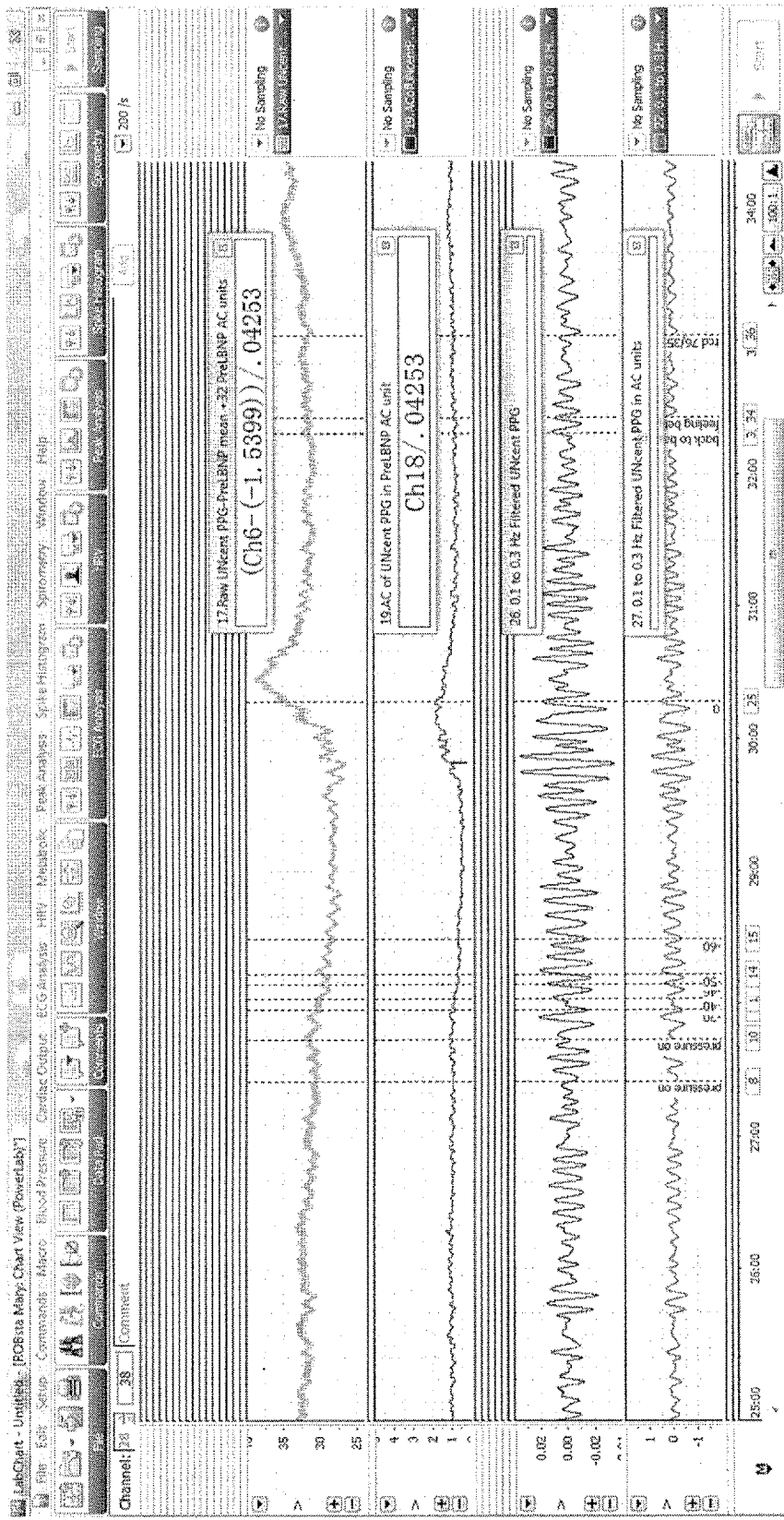
FIG. 11 shows additional manipulations of the AC$_{rest}$Mults tracing shown in FIG. 10. From top to bottom, channel 17=signal centered at 32 AC$_{rest}$Mults so as to center at typical preLBNP (i.e., at rest) DCblood value (DCblood$_{venous}$+DCblood$_{nonsvarterial}$); channel 19=AC component of the signal in AC$_{rest}$Mults: channel 26=oscillations within frequency range of DCblood that is affected by respiration at a frequency to 6 to 18 breaths/min shown centered at 0; channel 27=oscillations of channel 26 shown in AC$_{rest}$Mults to enable comparison with other photoplethysmographic components and parameters. As will be discussed in more detail with respect to spectral-domain analysis, conversion of AC and DC to AC$_{rest}$Mults shows that, whereas before impact of LBNP, AC greater than size of DC oscillations. However, during LBNP, AC drops to below at rest value, while amplitude of respiration-induced DC oscillations.

FIG. 11 shows a changed Y-axis crossing, to approximately 32 $AC_{rest}Mults$, to represent starting at full volume in the given subject as detailed below, thereby providing more relevant information than the raw voltage (see first channel of FIG. 10). The second channel (labeled 19) shows data of the AC channel after conversion to $AC_{rest}Mults$. The third channel shows continuous data after filtering at 0.1-0.3 Hz so as to focus on the section of DC predominantly influenced by respiration (but not the entire DC, which would be captured by looking at <0.5 Hz). The fourth channel shows how this can be expressed in $AC_{rest}Mults$. This enables viewing AC and DC in common units for such view, as well as for calculations (e.g., of relative magnitudes and variabilities in different study phases) and for spectral domain analysis (shown below).

TABLE 5

Desired, Established, Given and Sought Values for Uniform Display of Data in $AC_{rest}Mults$

| y = desired value in $AC_{rest}Mults$ of y-axis crossing | m = established conversion factor to convert data to $AC_{rest}Mults$ (=1 if data already in $AC_{rest}Mults$) | x = stable baseline (@rest) value of given photoplethysmograpic output | Solving for b, which is offset in $AC_{rest}Mults$ required to achieve desired y-axis crossing in $AC_{rest}Mults$ |
|---|---|---|---|
| If data already in $AC_{rest}Mults$: | | | |
| 0 $AC_{rest}Mult$ | 1 | Data in $AC_{rest}Mults$ | =−mx |
| 32 $AC_{rest}Mults$ | 1 | Data in $AC_{rest}Mults$ | =−mx + 32 |
| If data in volts: | | | |
| 0 $AC_{rest}Mult$ | 1 $AC_{rest}Mult/AC_{rest}Voltage$ | Data in Volts | =−mx |
| 32 $AC_{rest}Mults$ | 1 $AC_{rest}Mult/AC_{rest}Voltage$ | Data in Volts | =−mx + 32 |

Subsequent graphing of continuous tracing would generate "y" at each time point based on established "m" multiplied by changing "x" (i.e., changing photoplethysmographic values over time)+calculated "b" (as per Table 5).

FIGS. 7-9 demonstrate some of the options for such displays.

FIGS. 10 and 11 show how multiple configurations of the same signal can be displayed in synchrony. FIG. 10 shows It should be noted that the aforementioned text and descriptions have focused on voltages, $AC_{rest}Mults$, DCblood and compliance and related graphic displays. Much of the remainder of this section will focus on conversion of the photoplethysmographic signal to a measure of volume To further test whether the relationship between $DCblood_{rest}$ and $AC_{rest}$ of the photoplethysmograph measurement at the Forehead (PPG@FH) constitutes a microcosm of the relationship between capillovenous volume (CVV) and stroke volume (SV) of the systemic circulation and thereby adapt the photplethysmogram to quantify volume (in "$ml_{PPG}$"), I elected to convert hotoplethysmograph readings to measurements of volume. In a preferred embodiment to achieve this heretofore unattainable measurement, $AC_{rest}$ is converted to a volume measurement based upon a measured "$SV_{rest}$" in ml (e.g., by echocardiography) or estimated $SV_{rest}$ in ml (based upon population estimates from others who have undergone echocardiographic measurements). The PPG to volume conversion factor (CF) at rest for all data points is determined as follows:

--- a) For data already converted to $AC_{rest}$Mults:
   CF: $SV_{rest}$Volume/1$AC_{rest}$Mult
   Volume (in $ml_{PPG}$) for a given AC or DC measurement:
      = current # of $AC_{rest}$Mults × CF
      = current # of $AC_{rest}$Mults × '$SV_{rest}$in ml/1$AC_{rest}$Mult'
   And if $SV_{rest}$ is known, e.g. 125 ml, then
      = current # of $AC_{rest}$Mults × '125 ml/1$AC_{rest}$Mult'
b) One also could relate $SV_{rest}$Volume/$AC_{rest}$Voltage, such that Volume in $ml_{PPG}$:
      = current voltage × '$SV_{rest}$in ml/$AC_{rest}$Voltage'
   And if $SV_{rest}$ is known, e.g. 125 ml, then
      = current voltage × '125 ml/$AC_{rest}$Voltage'

---

The conversion is summarized in FIG. 12; a sample calculation is shown in FIG. 13.

As per displaying in $AC_{rest}$Mults in Table 5, establishment of a means for consistent display of photoplethysmographic data within and among subjects in $ml_{PPG}$ can be achieved with an inventive conversion factor and determination of the desired $ml_{PPG}$ value of y-axis crossing for DCblood (consisting of $DCblood_{venous}$ and $DCblood_{nonSV\,arterial}$) in $ml_{PPG}$ (Table 6). Assume measured SVrest=125 ml.

of 50% from $SV_{rest}$ would be accompanied by a decrease in $AC_{rest}$Mults by 50%. This relationship could be used as the basis for subsequent assessments in the absence an $AC_{rest}$-Voltage: one could record the $AC_{@GivenTimePoint}$ Voltage for the $SV_{@GivenTimePoint}$Volume, (i.e. for the SV used for calibration at the given time point). However, it would be preferable for interparameter, intersite and intersubject consistencies if $AC_{@GivenTimePoint}$Voltage was extrapolated to the "universal" $AC_{rest}$Voltage which then would correspond to 1 $AC_{rest}$Mult. In most cases, if the $SV_{rest}$ is not known from a prior echocardiographic measurement (e.g., in a cardiologist's office), then $SV_{rest}$ can be estimated from population values. Assuming that the value assigned to $SV_{rest}$=100 ml (as opposed to 125 in many of our robust volunteers) and that the $SV_{@GivenTimePoint}$=current SVstroke=70 ml, then the following relationship is established:

# of $AC_{@GivenTimePoint}$Mults/1 $AC_{rest}$Mult=70 ml/100 ml.

Hence, the $AC_{@GivenTimePoint}$Voltage would correspond to 0.7 $AC_{rest}$Mults. It can then be extrapolated to $AC_{rest}$Voltage as follows:

0.7/1=$AC_{@GivenTimePoint}$Voltage/$AC_{rest}$Voltage, where the $AC_{@GivenTimePoint}$Voltage is the current AC voltage.

Next, using an estimated $SV_{rest}$ of 125 ml (based upon measurements in young healthy subjects and other young, healthy subjects or the literature), inventive conversion is herein used to determine the $AC_{@rest}$ and DCblood $ml_{PPG}$ values for the six subjects in whom DCblood (in voltage and converted to $AC_{rest}$Mults) was determined by application of external pressure (as shown in FIG. 4). Since $AC_{rest}$ was established as equivalent to $SV_{rest}$, then 1 $AC_{rest}$Mult rep-

TABLE 6

Desired, Established, Given and Sought Values for Uniform Display of Data in mlppg

| y = desired value in $ml_{PPG}$ of y-axis crossing | m = established conversion factor to convert data to $ml_{PPG}$ (=1 if data already in $ml_{PPG}$) | x = baseline (@rest) value of given photoplethysmograpic output | Solving for b, which is offset in $ml_{PPG}$ required to achieve desired y-axis crossing in $ml_{PPG}$ |
|---|---|---|---|
| *If data already in $ml_{PPG}$:* | | | |
| 0 $ml_{PPG}$ | 1 | Data in $ml_{PPG}$ | =−mx |
| 4000 $ml_{PPG}$ | 1 | Data in $ml_{PPG}$ | =−mx + 4000 |
| *If data in $AC_{rest}$Mults:* | | | |
| 0 $ml_{PPG}$ | 125 ml/1 $AC_{rest}$Mult | Data in $AC_{rest}$Mults | =−mx |
| 4000 $ml_{PPG}$ | 125 ml/1 $AC_{rest}$Mult | Data in $AC_{rest}$Mults | =−mx + 4000 |
| *If data in volts:* | | | |
| 0 $ml_{PPG}$ | 125 ml/$AC_{rest}$Voltage | Data in Volts | =−mx |
| 4000 $ml_{PPG}$ | 125 ml/$AC_{rest}$Voltage | Data in Volts | =−mx + 4000 |

Subsequent graphing of continuous tracing would generate "y" at each time point based on established "m" multiplied by changing "x" (i.e., changing photoplethysmographic values over time)+calculated "b" (as per Table 6).

If a calibrating measurement was not previously obtained at rest, then as previously alluded to with reference to FIG. 2, it can be derived based upon the stroke volume at the given time point based on the aforementioned relationship that $SV_{rest}$=1 $AC_{rest}$Mult. The $SV_{@GivenTimePoint}$/$SV_{rest}$ corresponds to $AC_{@GivenTimePoint}$/$AC_{rest}$ (i.e., to the number of $AC_{rest}$Mults or fractions thereof) at given time point; i.e., in the absence of local distortions, a decrease in systemic SV resents 125 $ml_{ppg}$. DCblood conversion to volume was accomplished by two equivalent methods described above:
1) Conversion of DCblood voltage to # $AC_{rest}$Mults, with subsequent multiplication of # of $AC_{rest}$Mults by the aforementioned conversion factor ($SV_{rest}$/1 $AC_{rest}$Mult); or
2) Dividing $DCblood_{rest}$ voltage/$AC_{rest}$Voltage, with subsequent multiplication by $SV_{rest}$ Based on the aforementioned documentation that $DCblood_{venous}$=25.6±18.4 $AC_{rest}$Mults (according to the method shown in FIG. 4), this indicates that, if $SV_{rest}$=125 ml, then DCblood=~3200 $ml_{PPG}$. [As will be utilized in the context of lower body negative pressure, one also can calculate that the mean resting nonpulatile volume, which is virtually the entire systemic volume as =~125×32=~4000 ml$_{PPG}$] The reasonableness of this approach for assessing venous volume is supported by the literature: a classic text relates that the cumulative volume in systemic venous circulation is ~3250 ml, as distributed among capillaries (300 ml), venules (350), veins (2100), vena cavae (350) and right atrium (150) [Best C H and Taylor N B, *The Physiologic Basis of Medical Practice*, 8$^{th}$ ed, The Williams and Wilkins Co., Baltimore 1966; FIG. 36.1 A and 36.1 B.] To minimize bias, the literature was accessed after my determination based on the photoplethsmographic-derived volumes in accordance with the embodiments introduced herein.

Further suggestion that the present embodiments enable the forehead microvasculature to be viewed as a microcosm of the systemic circulation is the observation that the 'DCblood/AC' ratio of 25.6/1 under resting conditions at the Forehead (i.e., DC in AC$_{rest}$Mults) is comparable to to the systemic 'capillovenous ml/SV ml' ratio (3,250/125)=26). This was well within the 95% confidence limits (11.63) of the forehead ratio of 25.6±18.4.

Once the DC/AC relationship (e.g. ~25.6/1) has been established in a large number of healthy subjects, with potential adjustment for less robust individuals, then one could approximate relative as well as absolute changes in volume simply based on change in AC$_{rest}$Mults (i.e., changes in voltage relative to the AC$_{rest}$Voltage). Conversion to volume can be achieved by the inclusion of a measured or estimated stroke volume (as shown below in a model of simulated blood loss).

In a preliminary assessment of the universality of the DCblood$_{rest}$/AC$_{rest}$ relationship, the DCdecline in AC$_{rest}$Mults was also measured while applying pressure to the photoplethysmograph measurement at the Ear (PPG@Ear). This was more difficult to achieve than at the Forehead primarily as a consequence of movement artifact (which likely may be excluded through bioengineering such as inclusion of additional filters to identify specific tissues and substrates and by including means of artefact rejection). Zeroing at the Ear was accomplished by squeezing the photoplethysmograph and underlying lobe between two fingers (after covering the contralateral surface with black tape so as not to include the investigator's finger in the measurement field). Attempts to similarly displace blood from the finger were complicated by the thickness of the potential light path, thereby necessitating pronounced squeezing of the tissues and consequent reorientation of the photoplethysmograph during the zeroing process. An alternative method was therefore relied upon—with the arm held elevated at 90° for 30 seconds, I compressed the brachial artery until pulsations were no longer apparent; the DC decline amounted to DCblood. The DCblood/AC ratios were determined at the respective sites.

The likelihood of similar relationships throughout the body was suggested by the finding that DCblood/AC ratios based upon zeroing at the Ear and finger averaged ~24 AC$_{rest}$Mults and 22 AC$_{rest}$Mults, respectively (encouraging, especially since the finger is subject to greater autonomic impact).

Thus, the present invention has identified the means to and value of distinguishing AC and DC components of the photoplethysmograph and of limiting the impact of attenuation and background. Moreover, it also has provided means to achieve these aims with basic technologies. However, it should be appreciated by those experienced in this field that, now that the value of this has been shown, it would be of value to improve present means and develop additional means to implement the invention(s). The former may include improved filtering and artefact rejection and related means to improve the zeroing process; many such features are available in commercial devices (which could be modified to enable inactivation of autocentering and dynamic recalibrating algorithms). The latter may include other means that can be modified for separation of the AC and DCblood components introduced herein. Such isolation can be aided by, as well as enable, determination of the concentrations of substrates and metabolic products in the arterial and venous compartments. For example, the importance of distinguishing arterial and venous oxygen saturation has previously been emphasized; this would be facilitated by quantitative separation of AC and DCblood as described herein. Similarly, one could assess amounts of glucose and carbon dioxide. Conversely, if one knows amounts and concentrations in both vascular beds, s/he can determine relative volumes. Alternative means of separation include concurrent assessment of cell velocity (as by including principles of laser Doppler flowmetry). Additionally, one could refine study models to deliberately eliminate the arterial or venous component by focused component extinction.

2$^{nd}$ Series of Subjects: Simulated Systemic Hypovolemia with Lower Body Negative Pressure:

Documentation of the similarity between DC$_{rest}$/AC$_{rest}$ @Forehead (or Ear) and CVV$_{rest}$/SV$_{rest}$ of the systemic circulation led to postulation that, by converting photoplethysmograph voltage at a central site to ml$_{PPG}$, systemic blood loss during progressive hypovolemia (as opposed to simply locally induced changes) could be quantified. A progressive lower body negative pressure (LBNP) protocol was utilized because it enables progressive hypovolemia (typically commensurate to loss of 500 to 1500 ml) to be simulated in a noninvasive, readily reversible manner. In addition, in the absence of an established gold standard for directly quantifying blood loss (other than weighing buckets and sponges), the established correlation of degree of negative pressure with measured blood loss enabled testing photoplethysmographic determinations at specified degrees of lower body negative pressure (with established amounts of simulated loss and restoration thereof).

Twelve healthy volunteers ranging in age from 23 to 30 underwent a lower body negative pressure protocol which consisted of lying supine with the pelvis and hips in an airtight chamber. Monitoring included:
continuous EKG and continuous noninvasive finger arterial blood pressure;
three photoplethysmographs: noncentering, noncalibrating photoplethysmographs as described above The Ear was selected for central photoplethysmograph monitoring because it is a common site of pulse oximetry. After baseline measurements were obtained, negative pressure was progressively applied via the lower extremity chamber until one or more of the following safety endpoints:
light-headedness or other evidence of altered mental state;
decrease in blood pressure mean by >20%; or
change in heart rate of >50%.
subject discomfort Photoplethysmographic readings were recorded (and AC and DC components distinguished) at the Finger and Ear prior to the onset of ("pre") and during the challenge. Prior to analysis, AC@rest was recorded at each site and all voltages were subsequently converted to $AC_{rest}$Mults based upon the AC@rest at the given site in accordance with the present invention.

The rate of subsequent release of lower body negative pressure ("recovery") was titrated to improvement of signs and symptoms, while seeking to avoid precipitous rises in blood pressure and reflexive decline in heart rate.

In light of concerns that rapidly changing volume status and the impact of lower body negative pressure on breathing patterns, it was chosen not to rely on distinguishing AC and DC by the composite filtering used for the earlier micropatch investigation. Instead, as described in FIG. 2, a peak analysis module (LabChart 7.0, ADInstruments, Boulder Co.) was utilized to identify each beat and then isolate the peak and trough, with DC being taken as the trough and AC calculated as the "peak minus trough" difference for each identifiable beat. For purposes of this investigation, the minor difference between the DC determinations in the two series of subjects were disregarded.

Figure 16:
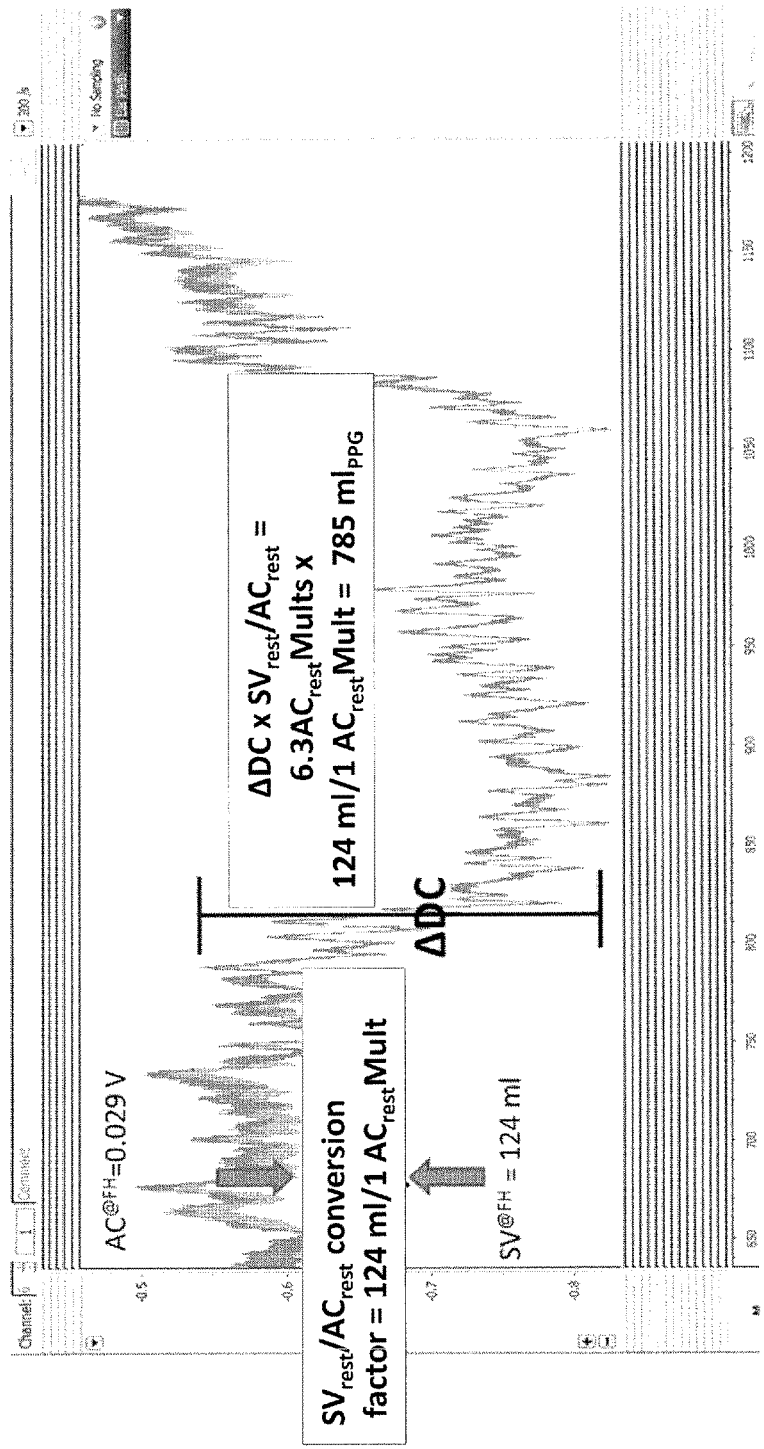
FIG. 16 is a graph of a photoplethysmograph on a subject undergoing lower body negative pressure which illustrates conversion of a decline in AC$_{rest}$Mults to a decline in volume based upon SV$_{rest}$Volume/1 AC$_{rest}$Mult conversion factor.
Figure 17:
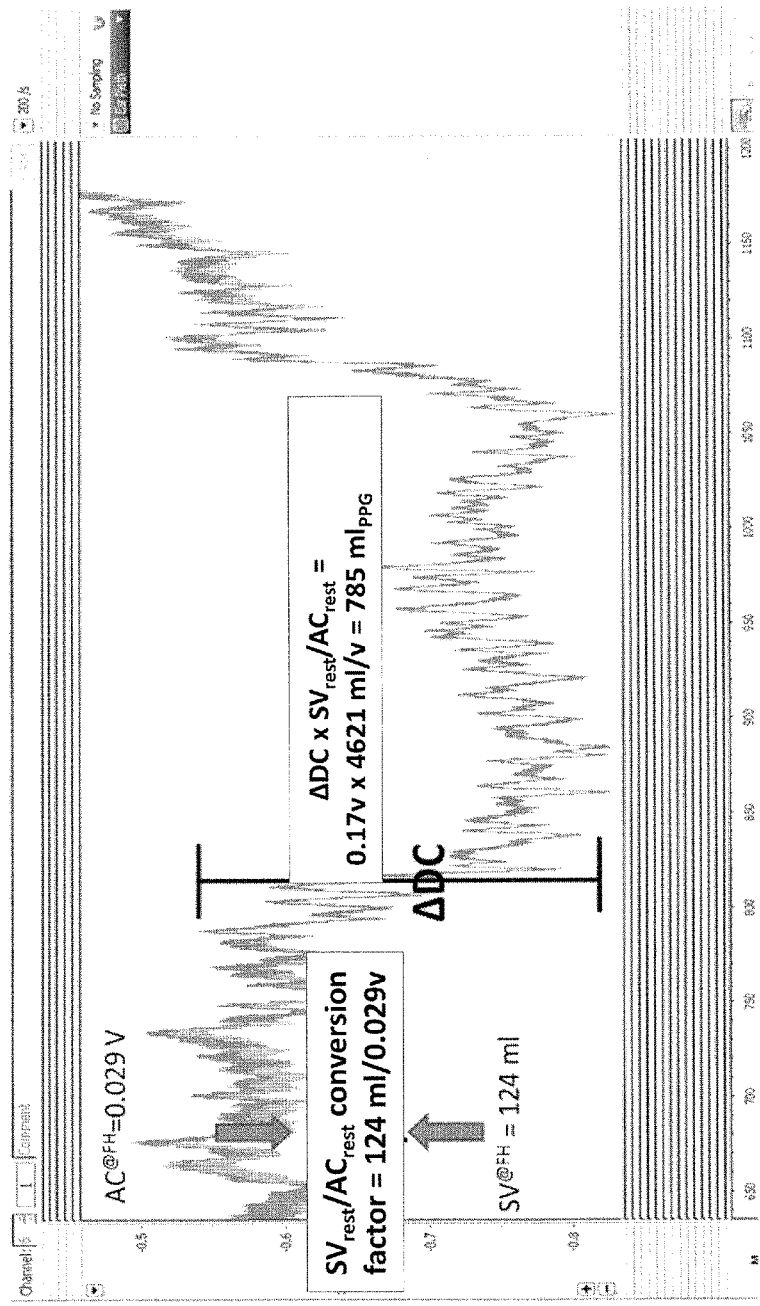
FIG. 17 is a graph of a photoplethysmograph on same subject undergoing lower body negative pressure which illustrates conversion of a decline in voltage to a decline in volume based upon SV$_{rest}$Volume/AC$_{rest}$Voltage conversion factor.

For each photoplethysmograph at a given site in a given subject, the voltage corresponding to the $AC_{rest}$Voltage was determined and each photoplethysmograph measurement was converted to $AC_{rest}$Mults and AC-derived volumes (in $ml_{ppg}$) as per aforementioned texts and figures. The $AC_{rest}$Mults values for AC and DC for the Ear photoplethysmograph and corresponding volumes were graphed continuously as new channels on the original time axis. (PPG@Finger was collected concurrently for subsequent assessment, discussed below). Examples of graphic display of the Ear photoplehysmographic in a single subject are shown in FIGS. 7-11 (described above). The methodology for conversion to volume is described above, with attention to FIGS. 12 and 13. Measurements during lower body negative pressure are determined per sample table shown in FIG. 15 and graphic displays of voltage to volume conversion for measurement of the amount of simulated blood loss (in $ml_{ppg}$) based upon $AC_{rest}$Mults and the $AC_{rest}$Voltage conversion factors are shown in FIGS. 16 and 17, respectively. In six of the subjects, $SV_{rest}$ was determined by echocardiography during the baseline phase. In the remaining subjects, the population mean of 125 ml was said to = $SV_{rest}$.

In addition to assessment of the overall photoplehysmographic signal, changes in AC and DCblood can be assessed separately in accordance with present invention. The mean±SD declines in AC $ml_{PPG}$ and DC $ml_{PPG}$ were compared to the LBNP-induced declines in stroke volume and overall systemic volume reported in the literature [Cooke W H, Ryan K L and Convertino V A. Lower body negative pressure as a model to study progression to acute hemorrhagic shock in humans. J Appl Physiol. 2004; 96:1249-61].

The decline in AC between baseline and the onset of light-headedness was determined and compared to baseline in $AC_{rest}$Mults as well as $ml_{ppg}$:
'↓AC in $AC_{rest}$Mults'/'$AC_{ore}$ in $AC_{rest}$Mults'=% ↓AC; or
'↓AC converted to $ml_{PPG}$'/'$AC_{rest}$ converted to $ml_{PPG}$'

The relative decline was compared to the relative decline in stroke volume obtained during prior investigations when measurements of stroke volume were obtained (with difficulty) by echocardiography during lower body negative pressure.

The decline in DC (in $AC_{rest}$Mults and converted to $ml_{PPG}$) likewise was determined between baseline and light-headedness. However, determination of relative ↓DC/$DC_{pre}$ required additional steps akin to those described in relation to FIG. 6 to eliminate the impact of background and thereby avoid a spuriously high denominator as a consequence of DCbackground. Based on Series #1 findings in accordance with the method of FIGS. 4 and 6, $DCblood_{pre}$ was assigned a value of 32 $AC_{rest}$Mults (to incorporate the entire systemic circulation). This value was based on the added ~6 $AC_{rest}$Mults decline associated with elimination of the arterial signal as per the method of FIG. 4, which was consistent with adding volumes within aorta (100 ml), arteries (300), arterioles (50) and heart (300), totaling ~750 ml to the 3250 ml cited above within capillaries, venules, veins, vena cavae and right atrium. Per the aforementioned conversion factor, the value of 32 $AC_{rest}$Mults estimated for $DCblood_{rest}$ (which also was $DCblood_{pre}$) was multiplied by the measured (or estimated) $SV_{rest}$Volume to generate baseline DC volume. (Although not elected for the series of subjects so as to avoid disturbance of the sensors, $DCblood_{pre}$ can be measured, as opposed to simply estimated, as for the methods used for and/or described in reference to Series #1 and shown in FIG. 4).

The decline in DC between baseline and the onset of light-headedness was determined and compared to baseline in $AC_{rest}$Mults as well as $ml_{ppg}$:
'↓DC in $AC_{rest}$Mults'/'$DCblood_{pre}$ in $AC_{rest}$Mults'=% ↓DC; or
'↓DC converted to $ml_{PPG}$'/'$DCblood_{pre}$ converted to $ml_{PPG}$'

Hence, in addition to estimating overall loss, the data permit comparison of relative venous and arterial decline. The photoplethysmograph based calculations were close to the simulated loss reported in the literature.

As noted in Table 7 below, the ΔAC/AC was -0.56±0.30 (mean±SD). This 56% decline, which was the same as a decrease of 0.56 $AC_{rest}$Mults, was close to the reported 65% ↓ in measured SV reported in the literature for similar degrees of lower body negative pressure. Conversion to volume indicated a decline in stroke volume of 70.0±37.5 $ml_{PPG}$.

The decline in DC averaged -7.73±3.65 $AC_{rest}$Mults. The ΔDC/$DCblood_{pre}$ constituted a 24% reduction from the -32 $AC_{rest}$Mults corresponding to nonpulsatile systemic blood prior to lower body negative pressure. The mean decline in DC was 14× greater than the decline in AC (=7.73/0.56). Conversion to volume indicated a decline in systemic volume of 966.3±456.39 $ml_{ppg}$. This is within the 500 to 1500 ml range of simulated loss reported in the literature for comparable degrees of lower body negative pressure. As discussed with respect to subjects during the recovery phase, intersubject variability may be attributable to different physiologic responses to the challenge.

TABLE 7

Declines in AC and DC and related volume conversions during lower body negative pressure

| Subjects | ΔBaseline | ΔAC | ΔAC/pre AC | ΔBaseline/ Pre AC | ΔBaseline/ ΔAC | Estimated Blood Withdrawal | Pre Stroke Volume |
|---|---|---|---|---|---|---|---|
| 1 | −0.181 | −0.022 | −0.758 | −6.334 | 8.359 | −791.740 | 124.0 |
| 2 | −0.440 | −0.020 | −0.541 | −11.938 | 22.050 | −1492.254 | |
| 3 | −0.185 | −0.033 | −0.736 | −4.150 | 5.638 | −518.700 | |
| 4 | −0.054 | −0.005 | −0.581 | −6.183 | 10.651 | −772.898 | 109.0 |
| 5 | −0.488 | −0.034 | −0.957 | −13.876 | 14.496 | −1734.519 | 103.0 |
| 6 | −0.154 | −0.003 | −0.113 | −5.917 | 52.431 | −739.682 | 164.0 |
| 7 | −0.031 | −0.001 | −0.236 | −5.716 | 24.222 | −714.532 | 126.0 |
| MEAN | −0.219 | −0.017 | −0.560 | −7.73 | 19.69 | −966.332 | 125.2 |
| STD | 0.18 | 0.01 | 0.30 | 3.65 | 15.98 | 456.39 | 23.78 |

Comment:
$SV_{rest}$ for subjects 2 and 3 estimated to be the mean value of 125 ml.

Figure 18:
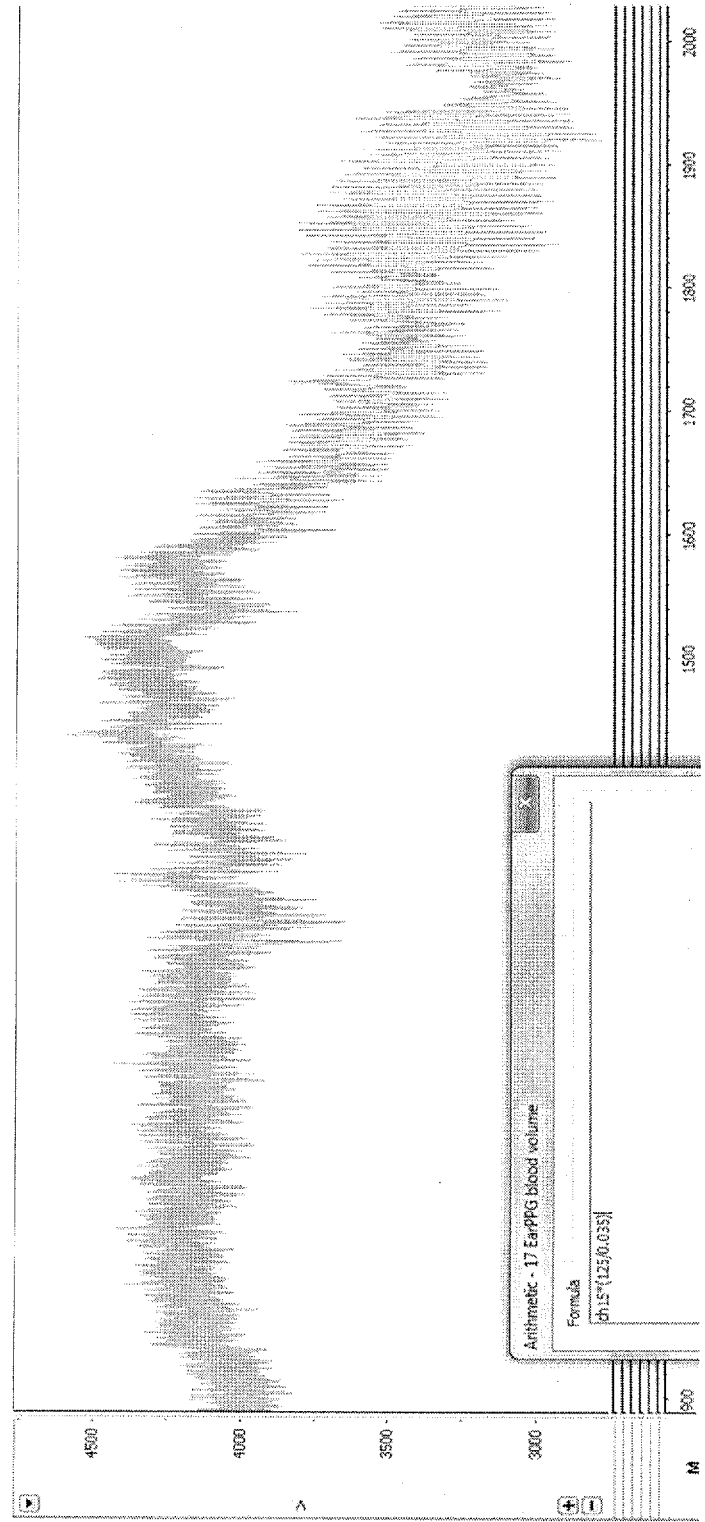
FIG. 18 shows graph of volume (in ml$_{PPG}$) generated by an ear photoplethysmograph during lower body negative pressure based upon converting voltage to ml$_{ppg}$ using inventive voltage to volume conversion factor and/or AC$_{rest}$Mult to volume conversion factor. Tracing (of channel 17) shows conversion of the PPGblood in channel 15 (shown in FIG. 5) to ml$_{ppg}$. This is achievable using either of the two voltage to volume conversion factors introduced herein.
Figure 19:
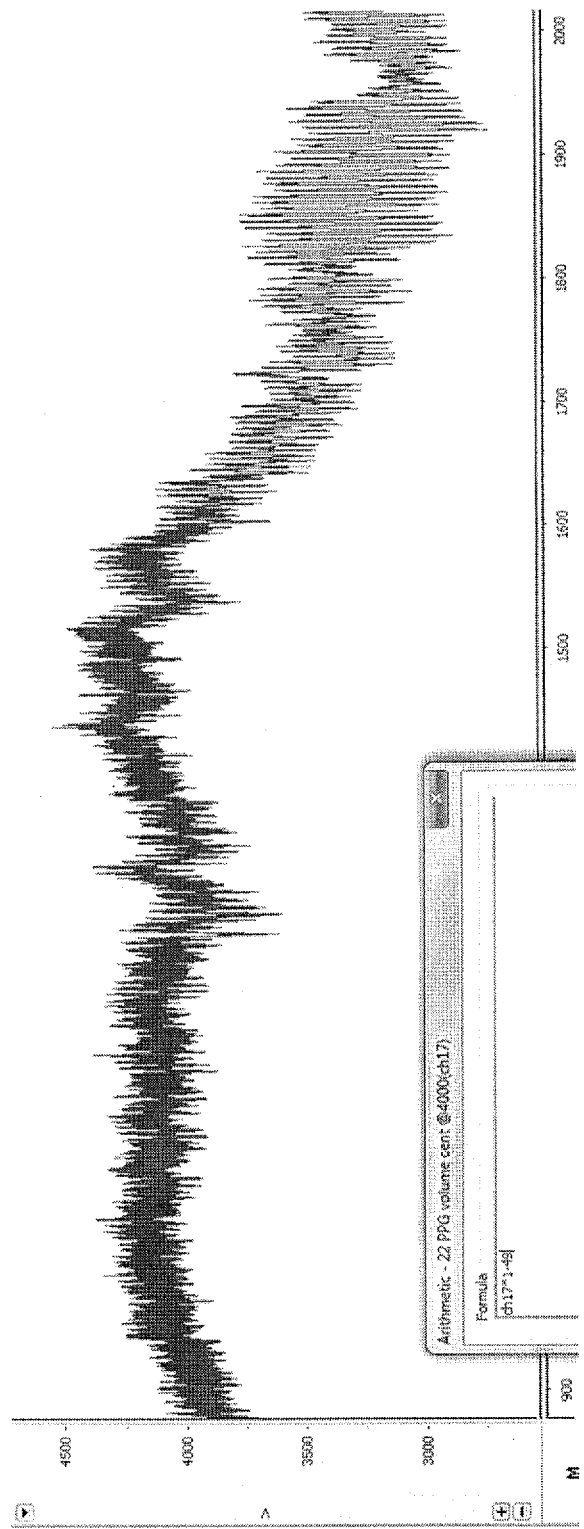
FIG. 19 shows that, if one wishes to standardize crossing point of y-axis for preLBNP volume (i.e., volume @rest) to 4000 ml$_{ppg}$ (based upon data shown herein) for the subject shown in FIG. 8, the offset for the present subject would be −49 ml$_{PPG}$. Tracing (channel 22 of representative data) showing signal of channel 17 (shown in FIG. 18) centered at 4000 ml$_{ppg}$, the value that would be obtained if the SV$_{rest}$=125 ml and we assume that DCblood=32 AC$_{rest}$Mults. This was obtained as follows: Mean DCblood for preLBNP interval was determined; the value, 4049 ml$_{ppg}$, was included as "x" component of y=mx=b for assumed straight baseline segment of the signal; solving for the offset ("b") with the equation: 4000=(1)×(4049)+b, determined that b=−49. Graphing equation for y intercept of 4000 then becomes. (1)×(channel 17)−49.
Figure 20:
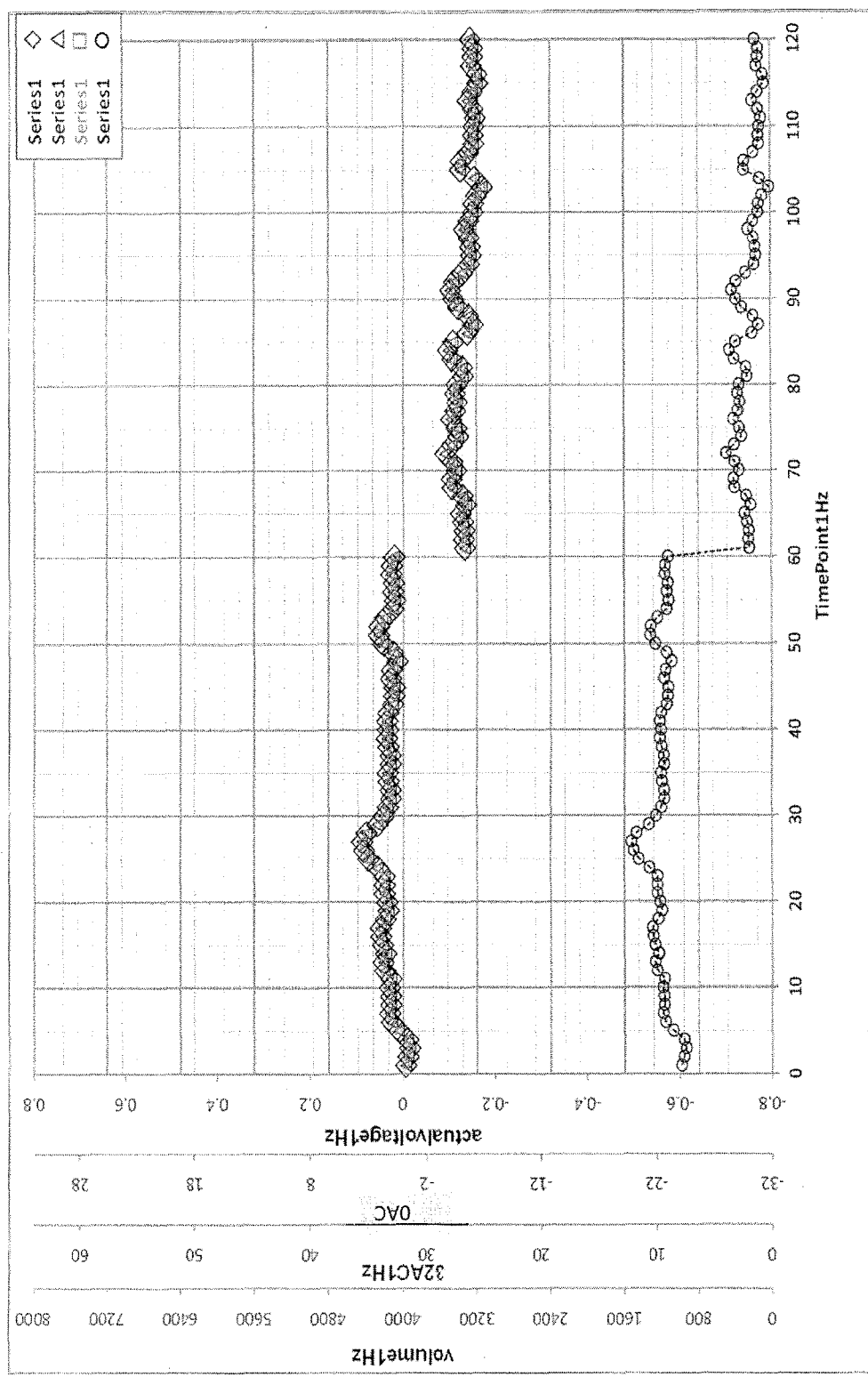
FIG. 20 shows multiple tracings graphed on multidimensional vertical axis. Multichannel graphing which illustrates consistency of inventive calculations and ability to simultaneously display determinations including actual voltage. $AC_{rest}$Mults centered at 0, $AC_{rest}$Mults centered at 32 and volume centered at 4000 $ml_{ppg}$. The latter 3 overlapped in every subject; voltage was isolated and its value differed among subjects.
Figure 21:
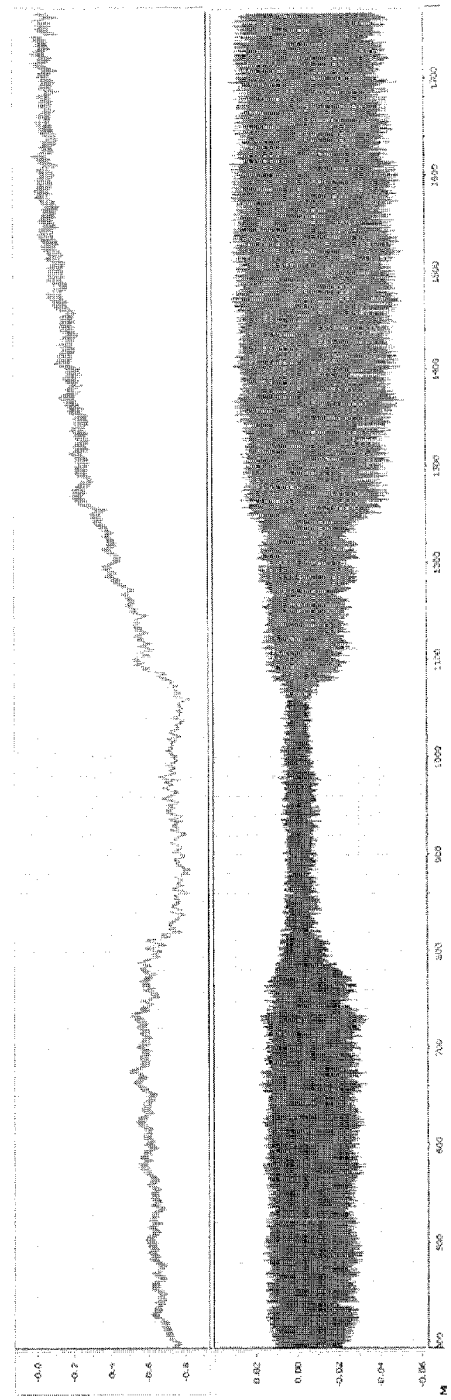
FIG. 21 shows the plethysmographic tracing at the Ear of a subject during baseline, application of negative pressure and recovery during a lower body negative pressure protocol.

FIGS. 18 and 19 show the changes in volume in a single subject. FIG. 20 integrates means of data display for a single subject on a single graph.

Recovery from Lower Body Negative Pressure:

The ability to distinguish AC and DC was during recovery upon release of lower body negative pressure would be vital to the management of patients with hypovolemia. These patients commonly first receive medical attention after significant blood loss already has occurred (e.g., trauma) and it is difficult to assess current status with respect to volume, vascular tone and cardiac function. This has prompted reliance on response studies, wherein the response to fluid administration is assessed (albeit with difficulty because of current inadequacies of monitoring). Restoration of systemic volume by release of lower body negative pressure (akin to volume infusion) provided a means to assess the utility of embodiments of the current invention.

During the recovery phase, the release segment (from lower body negative pressure off to maximum plethysmographic reading) was divided into 4-8 successive phases (based on duration of recovery and available window of suitable data). The AC and DC of each phase were determined by averaging 10-12 beats. Then ΔAC and ΔDC from baseline were calculated for each phase.

$$\Delta AC = (AC_{@GivenTimePoints} - AC_{rest})$$

$$\Delta DC = (DC_{@GivenTimePoints} - DC_{rest})$$

The values were expressed in $AC_{rest}$Mults and converted to $ml_{PPG}$ in accordance with aforementioned descriptions.

Figure 22:
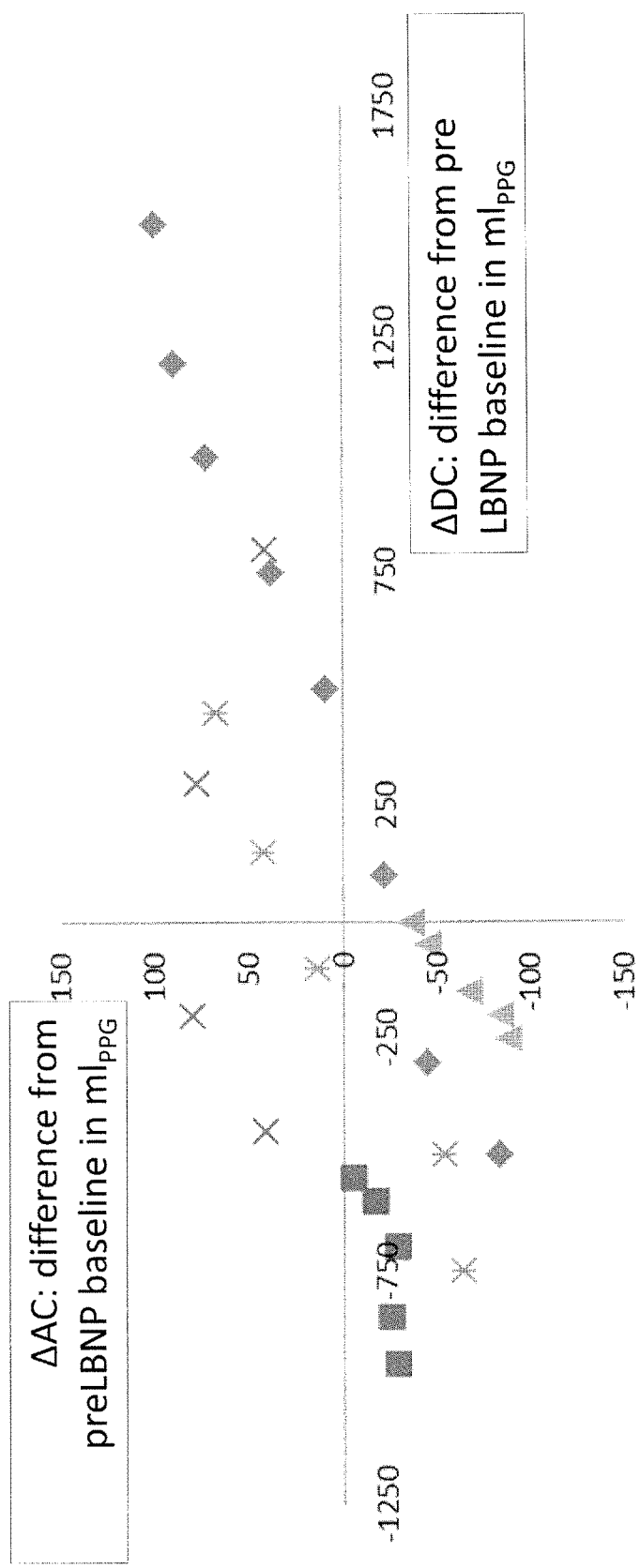
FIG. 22 shows the responses of AC and DC to release of negative pressure of FIG. 21 in five subjects.

FIGS. 22-27 show the application of, and potential utility of, independent and comparative assessment of AC and DC in $AC_{rest}$Mults and $ml_{ppg}$ in accordance with the present invention. In each of the five subjects for which segments of recovery are shown in FIG. 22, DC and AC increased upon progressive release of negative pressure. At the onset and early stages of recovery, all subjects were in the left lower quadrant, indicating that both DC (horizontal axis) and AC (vertical axis) were below preLBNP baseline values (consistent with hypovelmia). The rate and magnitude of recovery varied among subjects and between signal components. Intersubject variability was attributable to different degrees of negative pressure, different times of onset and different rates of release of negative pressure. Differences between AC and DC responses commonly revealed the bases for changes detected by other monitors and/or clinical signs; i.e., in addition to the hypovolemia of lower body negative pressure, the pattern of AC and DC responses may help distinguish cardiac factors (decreased cardiac function) and peripheral factors (altered vasomotor tone, local injury). Overshoot of restored volume return could be due to a number of factors, which would be identified by the relationship between AC and DC (e.g., hyperdynamic heart, local reflex hyperemia, injury induced hyperperfusion, hypervolemia). Patterns may be characterized by quadrant location (FIG. 22): upper right quadrant suggests that combination of fluid return and homeostatic mobilization from stores to mitigate the hypovolemic phase led to hypervolemia and augmented stroke volume (Rx, if any, might be a diuretic or vasodilator); upper left quadrant suggests increased contractility such that SV is greater than baseline even if systemic volume has not returned to normal (Rx may include judicious volume replacement, alteration of vasomotor tone or, if heart is undesirably hyperdynamic, use of an agent such as a beta-adrenergic blocker); lower right quadrant suggests compromise of cardiac contractility and/or intense arterial constriction such that AC is reduced despite replenishment of systemic volume (Rx may include increasing cardiac contractility).

Figure 23:
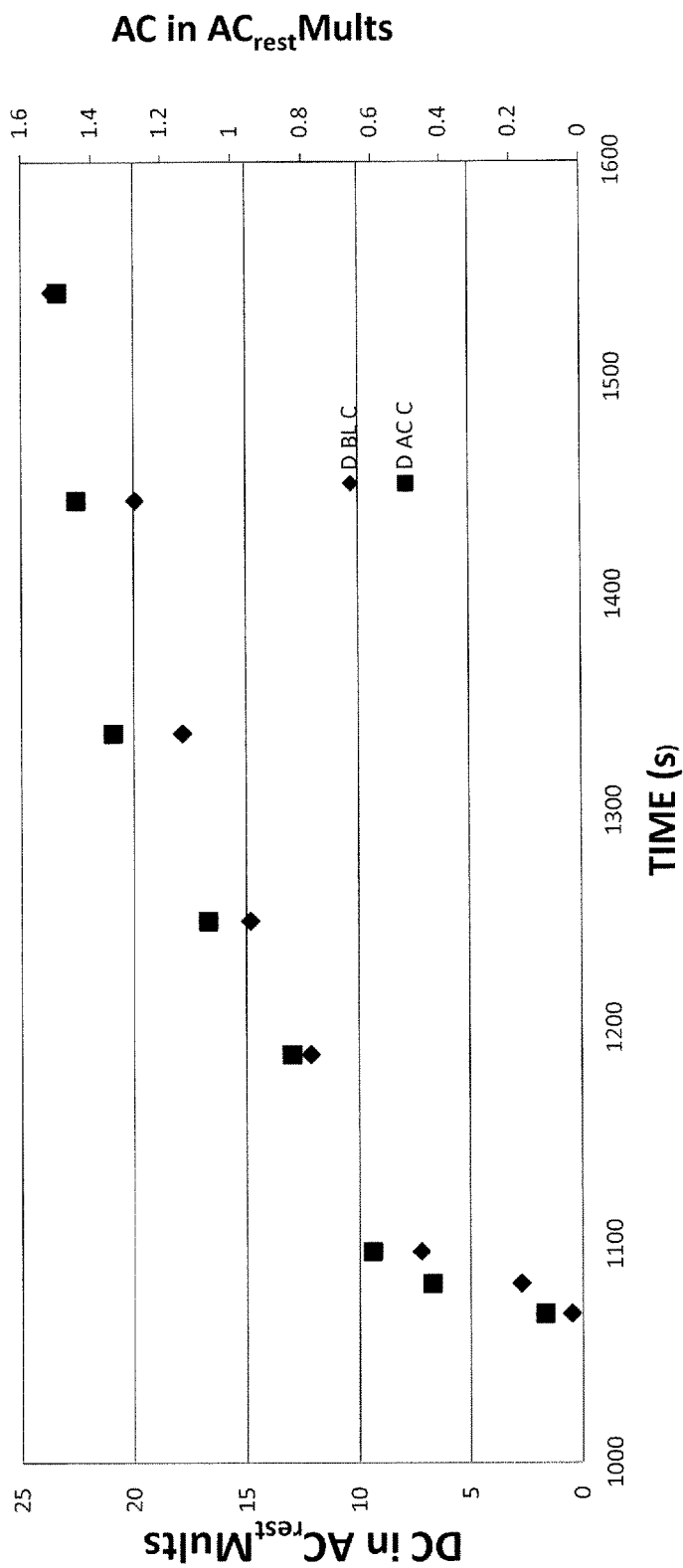
FIG. 23 shows the responses of AC and DC of a single subject in $AC_{rest}$Mults.
Figure 24:
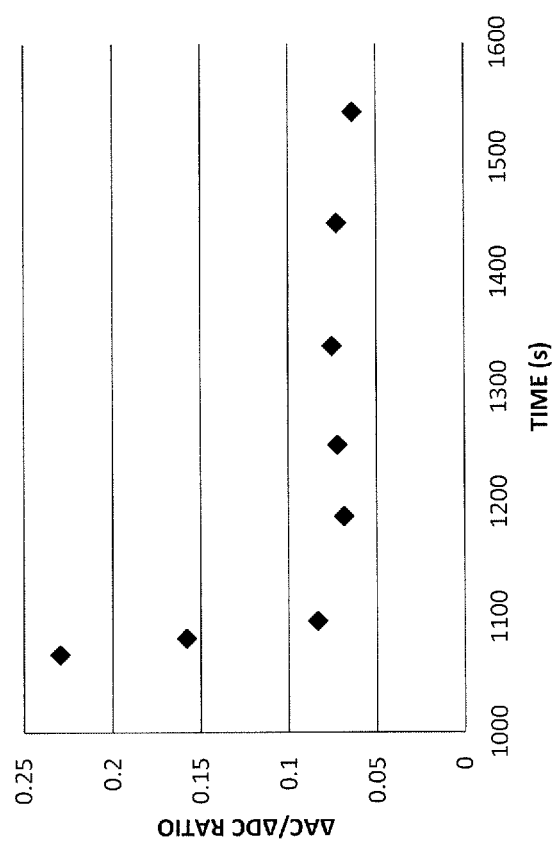
FIG. 24 shows ratio of ΔAC/ΔDC for data in FIG. 23.
Figure 25:
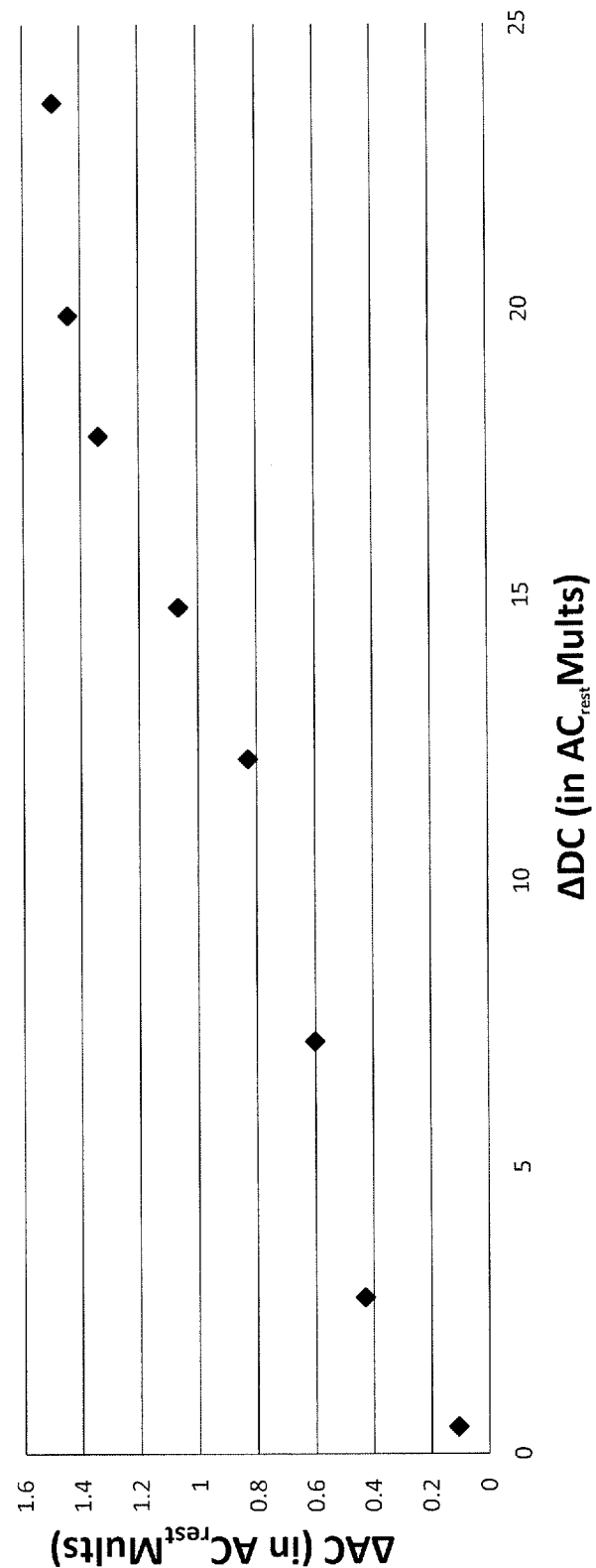
FIG. 25 shows how we can display relationship of AC and DC in a manner comparable to the Frank-Starling relationship for stroke volume and end diastolic volume.

The relationships between AC and DC (in $AC_{rest}$Mults) are shown for a single subject in FIGS. 23-25. Values represent increase from LBNP-induced nadir, which is assigned a value of 0. In FIG. 23, it is seen that the relative rate of rise in AC compared to DC is greatest upon initial return of sequestrated volume, indicating that the body is preferentially restoring stroke volume. The difference led to a return of AC to greater than baseline (as which time, $AC_{rest}$ was, by definition, 1 $AC_{rest}$Mult). FIG. 24 further depicts the changing relationship between AC and DC during recovery, with the initial ΔAC/ΔDC ratio of 0.23 reducing to 0.06 at the end of restoration. Of potentially greatest clinical significance, FIG. 25 shows a Frank-Starling relationship: during recovery, the subject is on the steep part of the curve with exaggerated ΔAC/ΔDC, consistent with the steep part of the Frank Starling curve where there is a robust response of SV for a given change in venous volume (evidenced as end diastolic volume in the classic Frank Starling curve).

Figure 26:
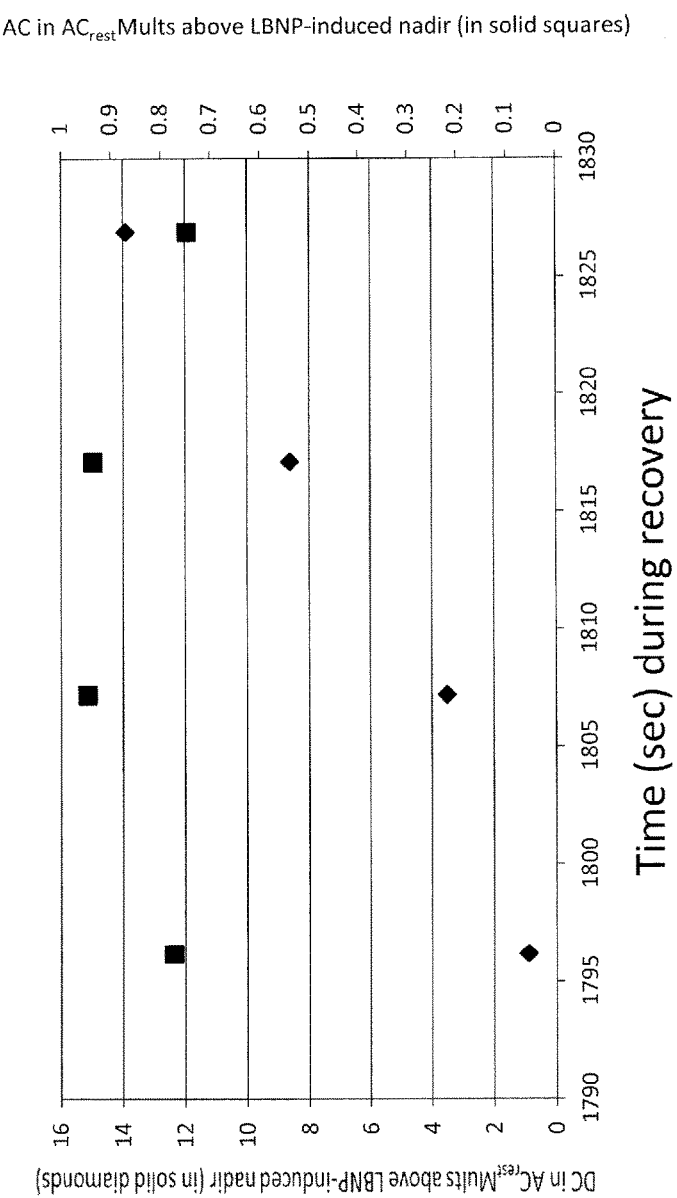
FIG. 26 shows AC and DC responses of a subject who developed light-headedness during return of blood sequestered in legs during lower body negative pressure.

In addition, the findings confirm that application of embodiments disclosed herein can provide valuable information as to the mechanisms associated with clinical signs and symptoms. FIG. 26 shows the recovery phase of a subject who became light-headed beginning at 1822 seconds. While overall systemic volume (DC, in diamonds) continued to increase, SV as measured by AC (solid squares) suddenly dropped.

Figure 27:
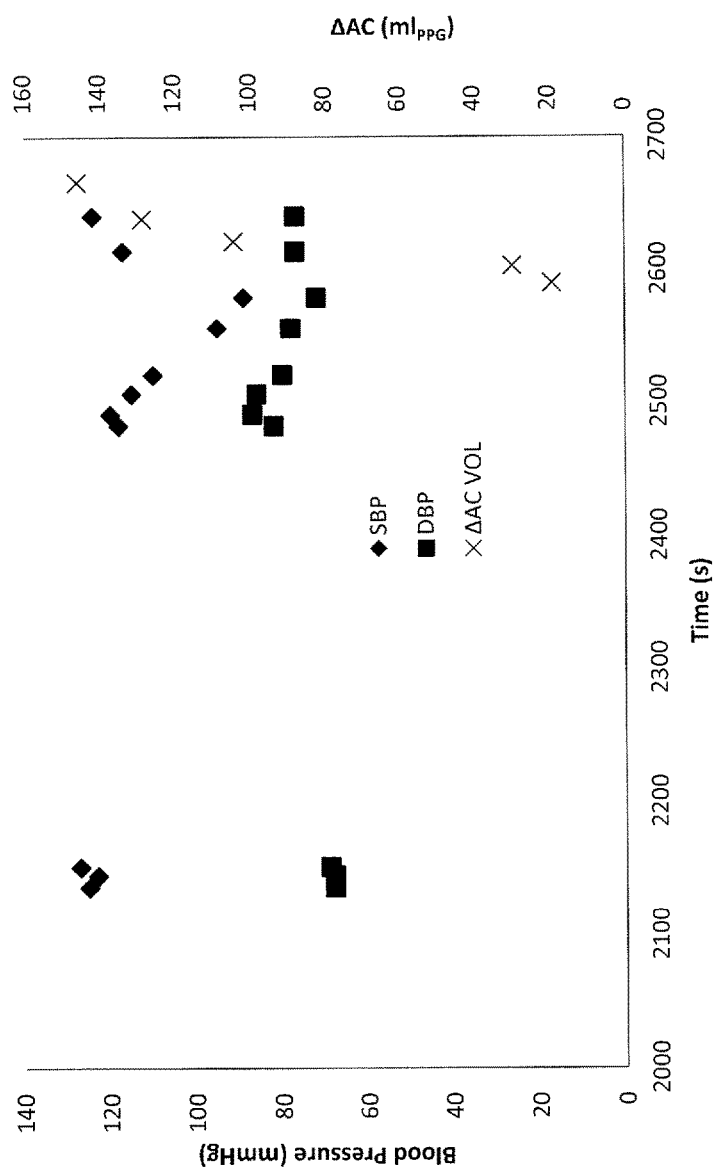
FIG. 27 shows AC changes in a subject who became hypotensive during return of blood sequestered in legs during lower body negative pressure.

FIG. 27 shows a subject in whom reinfusion was initiated at approximately 2450 seconds. After an initial rise in blood pressure, the systolic blood pressure declined from 120 mmHg to 82 mmHg. This was associated with a lack of increase in AC despite return of sequestrated blood (increase of DC). The relationship between AC and DC in this subject is also shown as the series of five star-like data points beginning at −60 ΔAC and −750 ΔDC in FIG. 22. Note that the increase in DC from −750 $ml_{PPG}$ to −500 $ml_{PPG}$ was associated with negligible increase in AC $ml_{PPG}$.

Finger Vs Ear Plethysmographic Changes During Lower Body Negative Pressure:

Application of the characterization of the AC and DC components of the plethsymographic signal in accordance with the present invention to multiple sites in a given subject (e.g., patient) offers the potential to multiply the benefits of inventive designs and methods. This is exemplified by data obtained concurrently at Ear and Finger during the aforementioned lower body negative pressure model, as summarized in FIG. 28. This shows the section of an Excel (Microsoft) spread sheet which contains data from 11 subjects who had concurrent Ear and Finger monitoring during our lower body negative pressure trial. The greater relative decline in the AC component (i.e., delivered stroke volume) of the Finger vs Ear is evidenced (in columns U and V) by their respective declines in AC height of 0.559 and 0.441 $AC_{rest}$Mults (where $AC_{rest}$Voltage is specific for given site); the decline at the Finger averaged 1.47× that at the Ear (col W). The greater relative decline in Finger vs Ear venous volume is evidenced by their respective declines of 8.02 and 2.46 $AC_{rest}$Mults (columns Y and Z); decline at the Finger averaged 3.95 times that at the Ear. These values may allow establishment of cutoffs for degrees of arterial constriction and venous constriction indicative of activation of homeostatic reflexes by severe hypovolemia. For example 10 of the 11 subjects had ↓DC @Finger that was at least 1.4 times greater than ↓DC@Ear, providing 1.4 as a tentative cutoff for identifying hypovolemia in an individual capable of a homeostatic response. While intersubject differences may provide valuable insight in patient characteristics (e.g., as per altered plethysmographic responses during reinfusion (FIGS. 26 and 27), confounding variability may be reduced with available artefact rejection algorithms and use of reference signals (not responsive to blood movement) that can improve the consistency of probe orientation at a given site.

Hence, the application of inventive embodiments at multiple sites enables comparisons with respect to the arterial and venous components of the circulation at the these sites in a previously unattainable manner in the clinical setting. The findings tell a story: as expected, the greater amount of arterial constriction at the finger causes a greater decline in its AC height; moreover, the greater decline in the DC component illustrates venous constriction at the finger, an indication of fluid mobilization from peripheral sites to offset the systemic hypovolemia induced by blood sequestration in the lower extremities during lower body negative pressure. It is reasonable to assume that the different changes at these sites reflect changes in regions with comparable innervation that are not accessible to noninvasive photoplethysmographic monitoring (e.g., brain, splancnic vasculature and kidney).

The data also permit additional analyses, including:
a) comparisons of the $\Delta AC/AC_{pre}$ ratios at the Ear and Finger—measuring the differences between Ear and Finger so as to enable determination of the fractions of the Finger decline that is attributable to systemic volume loss (that impacts Ear and Finger) or regional vasoconstriction (that predominantly impacts Finger), e.g., Δ@Finger–Δ@Ear and/or Δ/pre ratio at Finger–Δ/pre ratio at Ear b) comparison of the relative ↓DC at the different sites so as to assess the relative amount of homeostatic fluid mobilization (as would be coming not only from extremities such as the Finger but also internal regions such as the splancnic vasculature and spleen). The greater decline in DCblood in the Finger of the present series reveals mobilization that is consistent with the observation in the "responder" study above that return of the sequestrated fluid (in addition to the mobilized fluid) led to overshoot at the end of the restoration period.

As per the embodiments shown in FIGS. 4 and 6 and accompanying text, one also can normalize to the $DCblood_{pre}$ at the respective sites to obtain relative declines in DC as well as AC and to calculate changes in compliance.

Thus concurrent utilization of the AC and DC components in accordance with the present invention allows distinction, delineation and comparison of changes in the peripheral arterial and venous vasculature (vascular tone as well as volume). Resultant appreciation as to the impacts of hypovolemia per se and resultant changes in arterial and vasoconstriction can the guide therapy. For example, the greater decrease in DC@Finger reveals compensatory venous vasoconstriction that not only indicates the need for volume infusion but also can alert a health care provider that rapid replacement of all volume lost can lead to overshoot. Additionally, a disproportionate decrease in finger height reveals arterial constriction, indicating that the patient's blood pressure is being maintained by compensatory increase in vascular tone, which may be harmful to an organ such as the kidney. In the present series, application of embodiments introduced herein reveals that during lower body negative pressure most subjects evidenced decreased systemic volume, decrease stroke volume, venous constriction and arterial constriction. In more routine clinical settings, a patient's responses may be similarly assessed in the context of challenges such as the less extreme blood pooling associated with changing from a suprine to upright posture as well as in the context of vasoactive medications as may be titrated to treat chronic hypertension. As per FIGS. 26 and 27, abnormal responses may be most revealing.

In addition, as noted above, @rest values may be obtained at the onset of a challenge such as lower body negative pressure or days, weeks, months . . . before one is at risk of trauma or alternative compromise or intervention. As evidenced by the consistency of AC (described above), photoplethysmographic values remain consistent for a given sensor at a given site under resting conditions. Hence, @rest values for AC (as well as DC which maintained similar consistency) of one or more sensors on one or more subjects can be stored for a given probe and given station (for emission and processing) or for a group of uniform probes and stations.

Additional Applications of Meaningful Measurements:

A major benefit of the present invention is its conversion of often meaningless voltages to meaningful measures, these including $AC_{rest}$Mults, $AC_{rest}$Mult/mmHg compliance, and $ml_{PPG}$ measures of stroke volume and overall systemic volume.

This is particularly evident when one subjects data to what has been referred to as "black box" analysis because the analysis is performed by algorithms either hidden from or beyond the appreciation of most clinicians (and investigator). Spectral domain analysis is one such technique: it determines the contribution of a series of frequencies to the variance of a signal, traditionally by Fourier transformation; i.e., it determines the degrees to which oscillations at each of the frequencies within the given range contributes to overall signal variance. This technique has been recommended by my research team [Shelley K H, Shelley A, Silverman D G, Stout R G: Method of assessing blood volume using photoelectric plethysmography (U.S. Pat. No. 8,251,912; issued August 2012] and others for assessing the degree of variation in the photoplethysmographic signal attributable to respiration (typically between 0.1 and 0.3 Hz). However, that patent relied on relative changes, e.g., comparison of changes in DC at the respiratory frequency to oscillations of the AC components at the heart rate frequency (approximately (1 Hz) to provide a meaningful assessment. (Note, that prior to the present invention, relative measures of oscillatory-induced changes, not actual AC and DC values, were applied to patient assessment)

Figure 29:
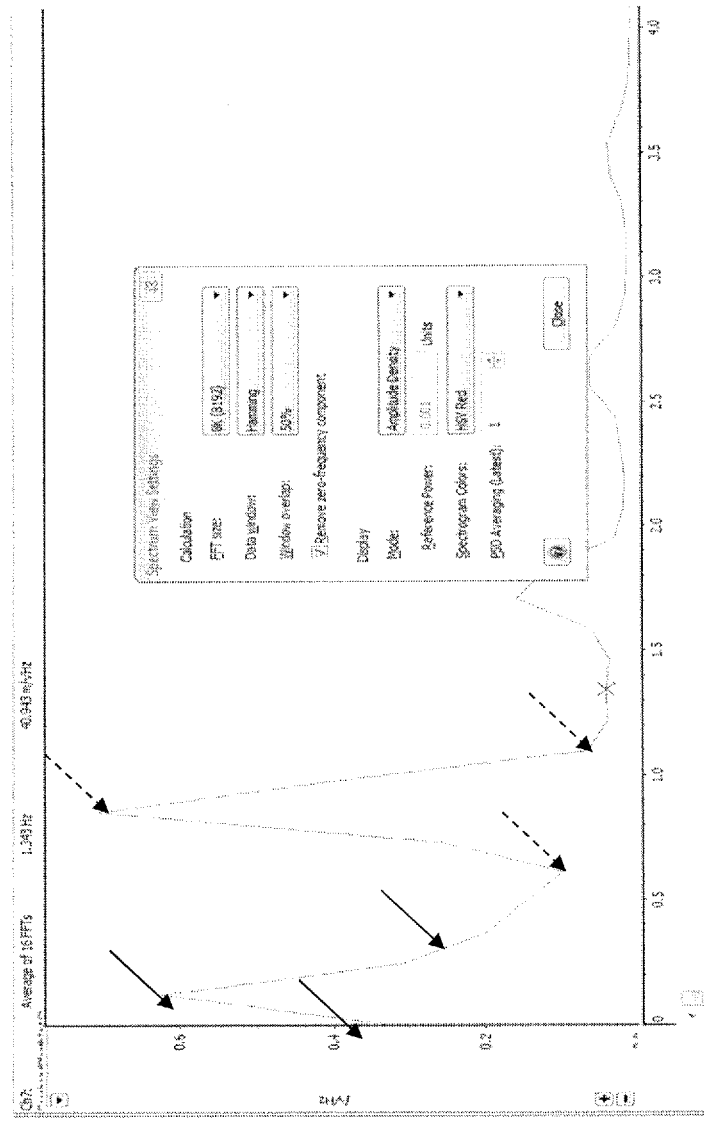
FIG. 29 shows the application of $AC_{rest}$Mults to provide heretofore unattainable clarity with respect to the delineation of data generated by spectral-domain analysis.
Figure 30:
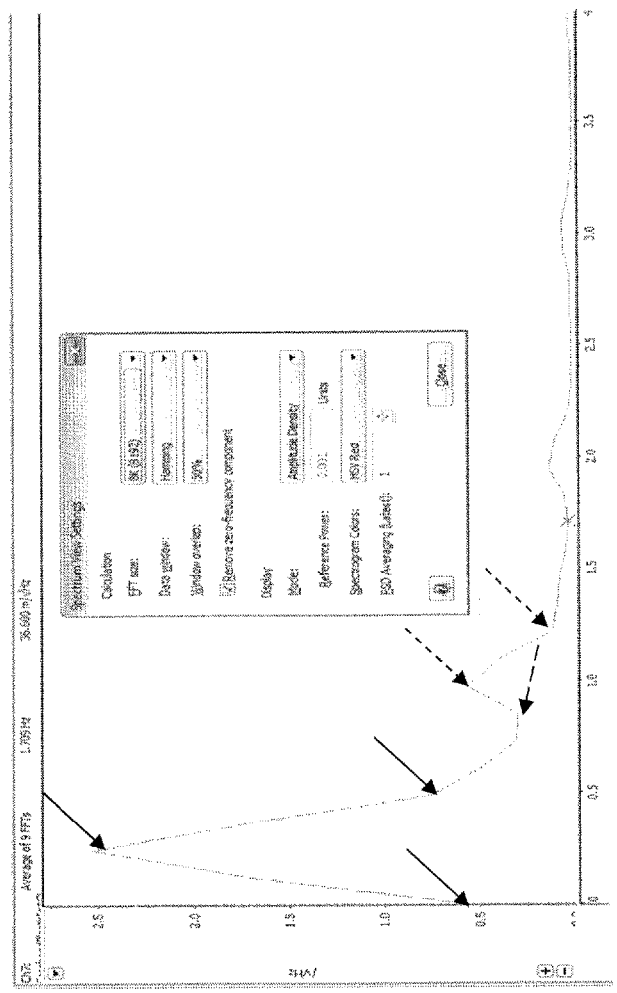
FIG. 30 shows the application of FIG. 29 to a subject breathing against a resistance so as to increase the impact of respiration on the distribution of venous blood volume.

FIGS. 29 and 30 show how conversion to $AC_{rest}$Mults provides heretofore unattainable meaning to spectral domain analysis of the plethysmographic waveform. Within the range of cardiac frequencies that are sampled at a given spectral resolution, it tells in readily appreciable units whether the stroke volume is <, =, or > than it was under resting conditions. In FIG. 29, we see that at the three frequency bands encompassing heart rate (at the given window width, sampling rate and FFT size), the heart rate oscillations (within the range of the subject's heart rate during the sampling period) have an amplitude density of 0.95 $AC_{rest}$Mults (0.10+0.70+0.075+0.075), wherein amplitude density integrates the frequencies within the frequency band in the immediate neighborhood of the given frequency. This indicates that the mean amplitude of the stroke volume (0.95 $SV_{rest}$Mults) is 95% of that obtained during @rest calibration. In addition, the data provide a measure of the volume displaced with respiration over the range of respiratory frequencies, that being ~1.17 $AC_{rest}$Mults (~0.35+ 0.62+0.2). This indicates that the change in central venous blood volume with each breath during spontaneous ventilation in this resting subject averaged 1.17 $AC_{rest}$Mults or 117% of the resting stroke volume.

The embodiments of the present invention facilitate comparison with data generated during breathing against a resistance so as to simulate positive pressure ventilation (as with a ventilator in an intubated patient). FIG. 30 shows that the increased pressure generated within the chest by breathing against a resistance displaced a much larger volume of blood from the chest to the periphery: ~2.9 $AC_{rest}$Mults (~0.6+1.5+0.8). This amount to 290% of $SV_{rest}$. Estimating $SV_{rest}$=125 ml, this amounts to displacement of ~360 ml, consistent with changes obtained with invasive monitoring during mechanical ventilation. FIG. 30 also shows that stroke volume increased with the increased activity of the subject, averaging ~1.4 $AC_{rest}$Mults (~0.5+0.6+0.3).

Figure 31:
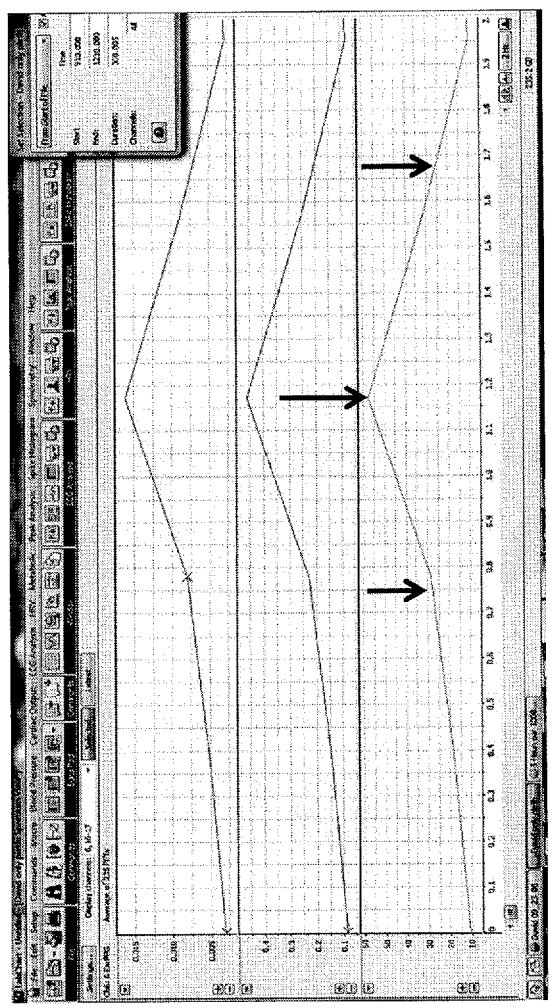
FIG. 31 is based on low frequency resolution of the spectral domain analysis display so as to illustrate the accuracy of $AC_{rest}$ Mults and $ml_{ppg}$ determinations.

FIG. 31 is from a different subject a few minutes after initial titration of negative pressure at the start of lower body negative pressure. Here, the frequency resolution has been reduced so that amplitudes of the spectral domain tracing can be readily summated around the cardiac frequency of a signal that has undergoing high pass filtering (>0.5 Hz) so as to eliminate respiratory induced changes in the DC component and thereby enable isolated viewing of AC. The findings confirm the accuracy of $AC_{rest}$Mults and data converted to $ml_{PPG}$ for assessment of stroke volume. The upper channel is the typical display based upon raw voltage. The middle channel shows that the AC component was equivalent to ~0.91 $AC_{rest}$Mults (~0.24+0.46+0.25). Likewise, the bottom channel shows that stroke volume was approximately 116 $ml_{ppg}$ (28+58+30).

Although not shown here, one could determine the impact of heart rate (Rwave to Rwave intervals) on the stroke volume; dividing the amplitude density at each of the three data points by the number of beats contributing to the given value would enable determination of rate-induced differences in volume (as may result from different durations for ventricular filling, which may be of particular importance during hypovolema). This is just of many applications that will soon become obvious to investigators and clinicians now that the vital tool(s) has been provided.

While the preferred embodiments have been shown and described, it will be understood that there is no intent to limit the invention by such disclosure, but rather, it is intended to cover all modifications and alternate constructions falling within the spirit and scope of the invention.

The invention claimed is:

1. A computer implemented method for photoplethysmograph measurement of volume status and changes, comprising:
   measuring photoplethysmographic values at a monitoring site under a resting condition;
   measuring photoplethysmographic values at a monitoring site in conjunction with application of a study agent;
   converting photoplethysmograph voltages, obtained from the steps of measuring photoplethysmographic values at a monitoring site under a resting condition and measuring photoplethysmographic values at a monitoring site in conjunction with application of the study agent, to measurements of volume change based on AC voltage at rest ($AC_{rest}$Voltage), wherein the steps of converting includes:
      referencing voltage change generated by portion of a stroke volume delivered to a given nonrecalibrating photoplethysmograph at a given site in a given subject under resting conditions to obtain an $AC_{rest}$-Calibration Voltage;
      establishing the $AC_{rest}$Calibration Voltage as equivalent to one $AC_{rest}$Multiple and resting stroke volume;
      applying the $AC_{rest}$Calibration Voltage to convert future AC values for given photoplethysmograph at a given site to $AC_{rest}$Multiples; and
      applying the $AC_{rest}$Calibration Voltage to convert DC values and changes thereof for given photoplethysmograph at a given site to $AC_{rest}$Multiples;
   comparing $AC_{rest}$Multiples determined based upon the steps of measuring photoplethysmographic values at a monitoring site under a resting condition and measuring photoplethysmographic values at a monitoring site in conjunction with application of the study agent thereby quantifying changes in pulsatile and non-pulsatile volume status of a local microcirculation to assess changes in local volume induced by the study agent when compared to a resting condition; and
   monitoring systemic cardiovascular status based upon the assessed changes in local volume.

2. The method according to claim 1, further including the step of applying a drug micro-patch to an individual prior to the step of measuring and comparing results to those obtained without the drug micro-patch.

3. The method according to claim 1, further including increasing pressure to an untreated control site causing progressive displacement of capillary, venous, arteriole and arterial blood to a point that vascular volume no longer contributes to a photoplethysmograph signal and measuring a photoplethysmograph signal wherein a drop in voltage until prior to loss of the pulsatile signal represents a blood contribution to a DC component of a photoplethysmographic signal and remaining non-pulsatile voltage represents a $DC_{background}$ component thereby distinguishing the blood contribution to a DC component of a photoplethysmographic signal from a nonblood background component of a DC signal.

4. The method according to claim 1, further including the step of measuring arterial and venous compliance at a monitoring site.

5. The method according to claim 1, further including the step of providing uniformly scaled data with common units of within subject and intersubject analyses.

6. The method according to claim 1, further including the step of augmenting information from other monitors and clinical signs with measurements of arterial and venous volume status, stroke volume, regional arterial and venous vasoconstriction/vasodilation.

7. The method according to claim 1, wherein the steps of measuring photoplethysmographic values under the resting condition and measuring photoplethysmographic values in conjunction with application of the study agent are performed at multiple sites.

8. The method according to claim 7, wherein the steps of measuring photoplethysmographic values under the resting condition and measuring photoplethysmographic values in conjunction with application of the study agent are performed at an ear, a forehead, or a finger.

9. The method according to claim 1, further including the step of converting $AC_{rest}$Voltage to a measurements of volume change based upon a resting stroke volume ($SV_{rest}$Volume), wherein the step of converting includes calculating a conversion factor that is equal to $SV_{rest}$Volume/1$AC_{rest}$Mult and multiplying a current number of $AC_{rest}$Mults by the conversion factor to determine the measurements of volume change.

10. A computer implemented method for photoplethysmograph measurement of volume status and changes, comprising:
  measuring photoplethysmographic values at a monitoring site;
  converting photoplethysmograph voltages to measurements of volume change based on AC voltage at rest ($AC_{rest}$Voltage), wherein the step of converting includes:
    referencing voltage change generated by portion of a stroke volume delivered to a given nonrecalibrating photoplethysmograph at a given site in a given subject under resting conditions to obtain an $AC_{rest}$Calibration Voltage;
    establishing the $AC_{rest}$Calibration Voltage as equivalent to one $AC_{rest}$Multiple and distribution of resting stroke volume;
    applying the $AC_{rest}$Calibration Voltage to convert future AC values for given photoplethysmograph at a given site to $AC_{rest}$Multiples; and
    applying the $AC_{rest}$Calibration Voltage to convert DC values and changes thereof for given photoplethysmograph at a given site to $AC_{rest}$Multiples; and
  comparing $AC_{rest}$Multiples determined based upon the step of measuring photoplethysmographic values at a monitoring site thereby quantifying changes in pulsatile and non-pulsatile volume status of a local microcirculation to assess changes in local volume; and
  monitoring systemic cardiovascular status based upon the assessed changes in local volume to identify and monitor hypovolemic conditions.

11. The method according to claim 10, further including increasing pressure to an untreated control site causing progressive displacement of capillary, venous, arteriole and arterial blood to a point that vascular volume no longer contributes to a photoplethysmograph signal and measuring a photoplethysmograph signal wherein a drop in voltage until prior to loss of the pulsatile signal represents a blood contribution to a DC component of a photoplethysmographic signal and non-pulsatile voltage represents a $DC_{background}$ component thereby distinguishing the blood contribution to a DC component of a photoplethysmographic signal from a nonblood background component of a DC signal.

12. The method according to claim 10, further including the step of measuring arterial and venous compliance at a monitoring site.

13. The method according to claim 10, further including the step of providing uniformly scaled data with common units of within subject and intersubject analyses.

14. The method according to claim 10, further including the step of augmenting information from other monitors and clinical signs with measurements of arterial and venous volume status, stroke volume, regional arterial and venous vasoconstriction/vasodilation.

15. The method according to claim 10, wherein the step of measuring photoplethysmographic values is performed at an ear, a forehead, or a finger.

16. The method according to claim 10, further including the step of converting $AC_{rest}$Voltage to a volume measurement based upon a resting stroke volume ($SV_{rest}$Volume), wherein the step of converting includes calculating a conversion factor that is equal to $SV_{rest}$Volume/1$AC_{rest}$Mult and multiplying a current number of $AC_{rest}$Mults by the conversion factor to determine the volume measurement.

17. A computer implemented method for photoplethysmograph measurement of volume status and changes, comprising:
  measuring photoplethysmographic values at a monitoring site to determine AC voltage at a given point in time ($AC_{@GivenTimePoint}$Voltage);
  measuring stroke volume to determine stroke volume at a given point in time ($SV_{@GivenTimePoint}$);
  estimating stroke volume at rest ($SV_{@rest}$) based upon population values;
  determining AC voltage at rest ($AC_{rest}$Voltage) based upon a $SV_{@GivenTimePoint}$, $AC_{@GivenTimePoint}$Voltage, and $SV_{@rest}$;
  converting photoplethysmograph voltages to measurements of volume change based on $AC_{rest}$Voltage, wherein the step of converting includes:
    referencing voltage change generated by portion of a stroke volume delivered to a given nonrecalibrating photoplethysmograph at a given site in a given subject under resting conditions to obtain an $AC_{rest}$Calibration Voltage;
    establishing the $AC_{rest}$Calibration Voltage as equivalent to one $AC_{rest}$Multiple and distribution of resting stroke volume;
    applying the $AC_{rest}$Calibration Voltage to convert future AC values for given photoplethysmograph at a given site to $AC_{rest}$Multiples; and
    applying the $AC_{rest}$Calibration Voltage to convert DC values and changes thereof for given photoplethysmograph at a given site to $AC_{rest}$Multiples; and comparing $AC_{rest}$Multiples determined based upon the step of measuring photoplethysmographic values at a monitoring site thereby quantifying changes in pulsatile and non-pulsatile volume status of a local microcirculation to assess changes in local volume; and monitoring systemic cardiovascular status based upon the assessed changes in local volume to identify and monitor hypovolemic conditions.

18. The method according to claim 17, further including the step of measuring arterial and venous compliance at a monitoring site.

19. The method according to claim 17, further including the step of providing uniformly scaled data with common units of within subject and intersubject analyses.

20. The method according to claim 17, further including the step of augmenting information from other monitors and clinical signs with measurements of arterial and venous volume status, stroke volume, regional arterial and venous vasoconstriction/vasodilation.

21. The method according to claim 17, wherein the step of measuring photoplethysmographic values is performed at an ear and a forehead.

\* \* \* \* \*